(12) United States Patent
Mohan Rao et al.

(10) Patent No.: US 8,835,635 B2
(45) Date of Patent: Sep. 16, 2014

(54) AMORPHOUS FORM OF VILAZODONE HYDROCHLORIDE SUBSTANTIALLY FREE OF CRYSTALLINE FORMS

(71) Applicants: Dodda Mohan Rao, Hyderabad (IN); Aadepu Jithender, Hyderabad (IN)

(72) Inventors: Dodda Mohan Rao, Hyderabad (IN); Aadepu Jithender, Hyderabad (IN)

(73) Assignee: Symed Labs Limited (IN)

( * ) Notice: Subject to any disclaimer, the term of this patent is extended or adjusted under 35 U.S.C. 154(b) by 0 days.

(21) Appl. No.: 13/656,882

(22) Filed: Oct. 22, 2012

(65) Prior Publication Data
US 2013/0324554 A1    Dec. 5, 2013

Related U.S. Application Data

(60) Provisional application No. 61/667,102, filed on Jul. 2, 2012.

(30) Foreign Application Priority Data

Jun. 5, 2012  (IN) .......................... 2242/CHE/2012

(51) Int. Cl.
```
A61K 31/497      (2006.01)
C07D 403/00      (2006.01)
C07D 405/12      (2006.01)
C07D 405/14      (2006.01)
A61K 31/496      (2006.01)
```
(52) U.S. Cl.
CPC ............ *C07D 405/14* (2013.01); *C07D 405/12* (2013.01); *A61K 31/496* (2013.01)
USPC ..................................... 544/373; 514/254.09

(58) Field of Classification Search
None
See application file for complete search history.

(56) References Cited

U.S. PATENT DOCUMENTS

| 5,532,241 | A | 7/1996 | Bottcher et al. |
| 7,381,726 | B2 * | 6/2008 | Bathe et al. ................ 514/252.1 |
| 7,981,894 | B2 * | 7/2011 | Bathe et al. ................ 514/252.1 |
| 8,193,195 | B2 * | 6/2012 | Bathe et al. .............. 514/254.09 |
| 8,236,804 | B2 * | 8/2012 | Bathe et al. ................ 514/252.1 |
| 8,318,744 | B2 * | 11/2012 | Bathe et al. ................ 514/252.1 |
| 2005/0163855 | A1 * | 7/2005 | Cho et al. ...................... 424/486 |

FOREIGN PATENT DOCUMENTS

| WO | WO9932118 | * | 1/1999 |
| WO | 2012102794 A2 | | 12/2002 |
| WO | 2012131706 A1 | | 10/2012 |
| WO | WO 201213170 A1 | * | 10/2012 |

OTHER PUBLICATIONS

Petit et al., The Amorphous State, 2006, Polymorphism in the Pharmaceutical Industry, 259-285.*
Timo Heinrich, et al. Synthesis and Structure—Activity Relationship in a Class of Indolebutypiperazines as Dual 5-HT1A Receptor Agonists and Serotonin Reuptake Inhibitors, J. Med. Chem. 2004, 47, 4684-4692.
Tsutomu Konno, Physical and Chemical Changes of Medicinals in Mixtures with Adsorbents in the Solid State, IV. Study on Reduced-Pressure Mixing for Practical USe of Amorphous Mixtures of Flufenamic Acid, Chem, Pharm. Bull. 38(7)2003-2007(1990).
United States Pharmacopeia, pp. 813-814, USP 31, NF-26, 2008.

* cited by examiner

*Primary Examiner* — Dennis Heyer
*Assistant Examiner* — Daniel M Podgorski
(74) *Attorney, Agent, or Firm* — Caesar, Rivise, Bernstein, Cohen & Pokotilow, Ltd.

(57) ABSTRACT

Disclosed herein is a stable amorphous form of vilazodone hydrochloride substantially free of crystalline forms, a process for the preparation, pharmaceutical compositions, and methods of treating thereof. Disclosed also herein are stable amorphous co-precipitates of vilazodone hydrochloride and a pharmaceutically acceptable excipient, methods for the preparation, pharmaceutical compositions, and method of treating thereof.

6 Claims, 16 Drawing Sheets

Figure 1: Powder X-ray diffraction (XRPD) pattern of Amorphous Form of Vilazodone Hydrochloride obtained according to the Example 1

Figure 3: Powder X-ray diffraction (XRPD) pattern of Amorphous Form of Vilazodone Hydrochloride obtained according to the Example 2

Figure 5: Powder X-ray diffraction (XRPD) pattern of Amorphous Form of Vilazodone Hydrochloride obtained according to the Example 4

Figure 6: Powder X-ray diffraction (XRPD) pattern of Amorphous Form of Vilazodone Hydrochloride obtained according to the Example 5

Figure 7: Powder X-ray diffraction (XRPD) pattern of Amorphous Co-precipitate of Vilazodone Hydrochloride with Polyvinylpyrrolidone (1:10)

Figure 9: Powder X-ray diffraction (XRPD) pattern of Amorphous Co-precipitate of Vilazodone Hydrochloride with Polyvinylpyrrolidone (1:5)

Figure 11: Powder X-ray diffraction (XRPD) pattern of Amorphous Co-precipitate of Vilazodone Hydrochloride with Hypromellose phthalate (1:10)

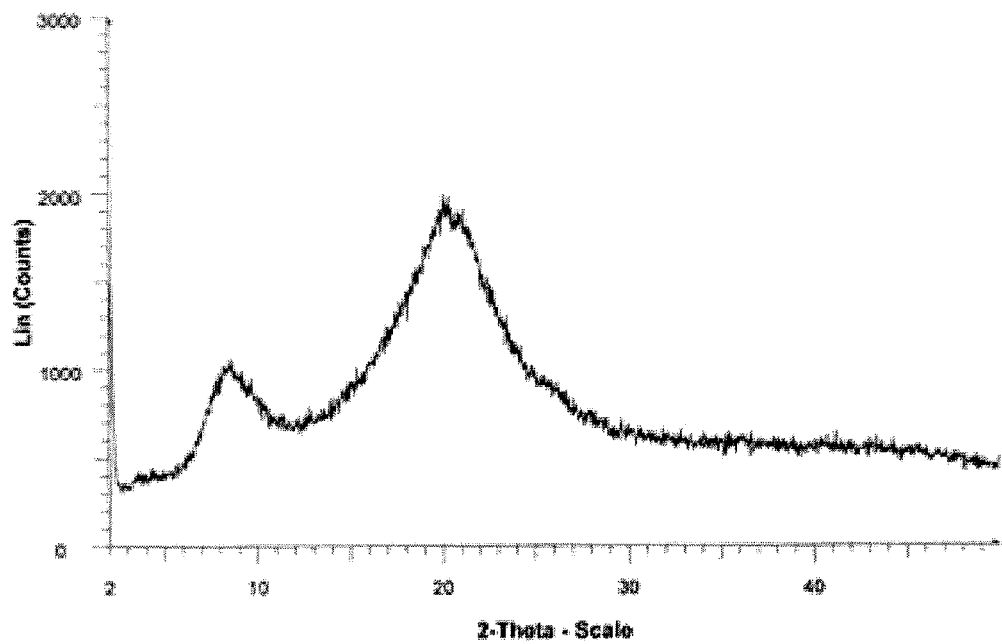
Figure 13: Powder X-ray diffraction (XRPD) pattern of Amorphous Co-precipitate of Vilazodone Hydrochloride with Hydroxypropyl cellulose (1:15)

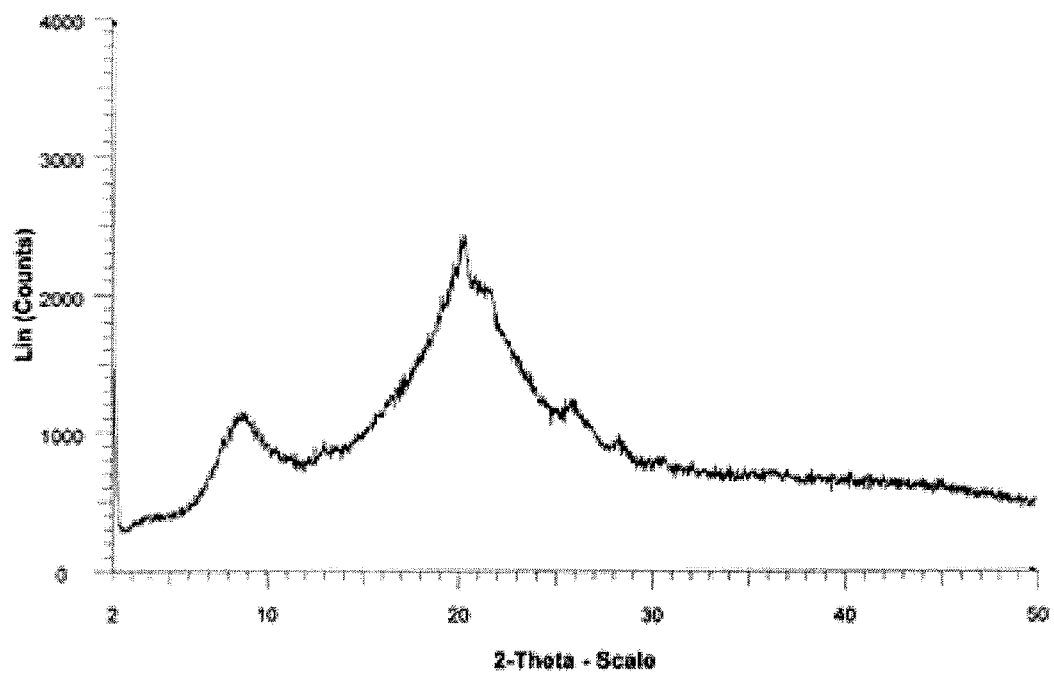
Figure 14: Powder X-ray diffraction (XRPD) pattern of Amorphous Co-precipitate of Vilazodone Hydrochloride with Hydroxypropyl cellulose (1:10)

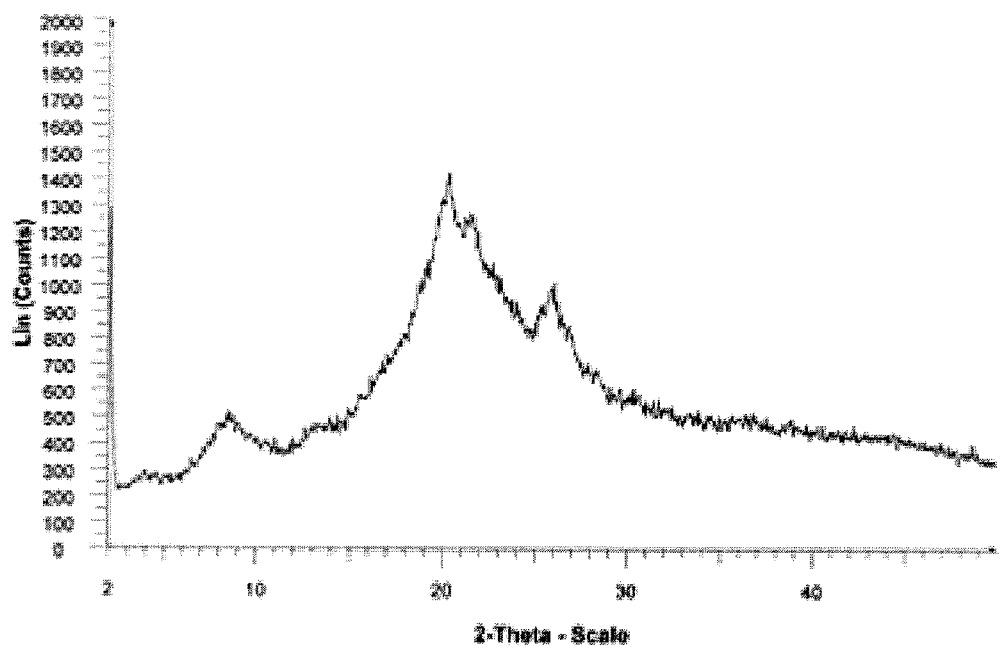
Figure 15: Powder X-ray diffraction (XRPD) pattern of Amorphous Co-precipitate of Vilazodone Hydrochloride with Hydroxypropyl cellulose (1:2)

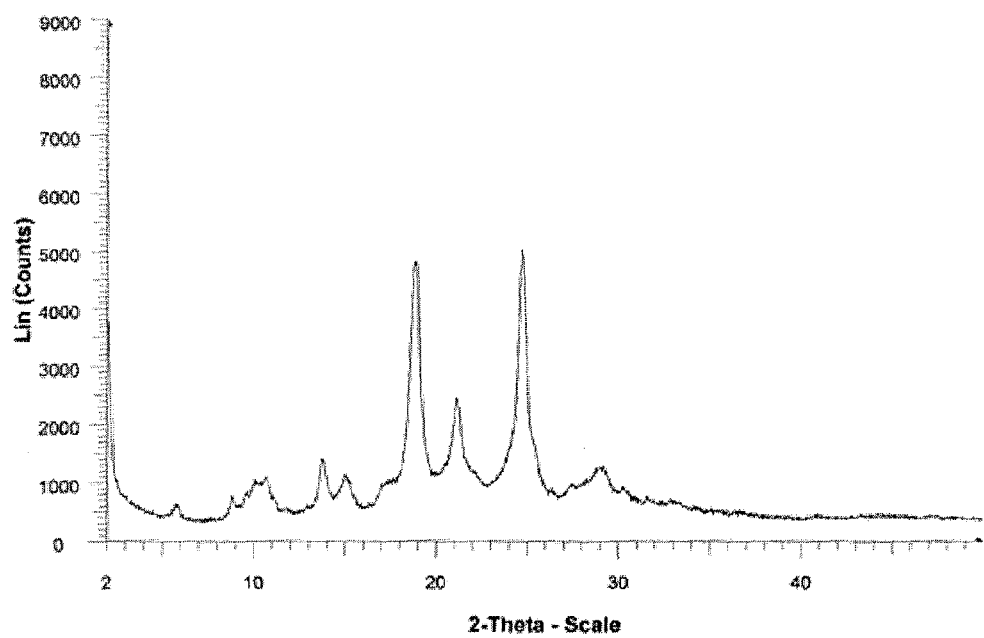
Figure 16: Powder X-ray diffraction (XRPD) pattern of Solid State Form (Form A) of Vilazodone Hydrochloride obtained according to the Reference Example

AMORPHOUS FORM OF VILAZODONE HYDROCHLORIDE SUBSTANTIALLY FREE OF CRYSTALLINE FORMS

CROSS REFERENCE TO RELATED APPLICATION

This patent application claims the benefit of priority to Indian Provisional Patent Application No. 2242/CHE/2012, filed on Jun. 5, 2012, and U.S. Provisional Patent Application No. 61/667,102 filed on Jul. 2, 2012, which are incorporated herein by reference in their entirety.

FIELD OF THE INVENTION

The present invention relates to a stable and highly pure amorphous form of vilazodone hydrochloride substantially free of crystalline forms, processes for the preparation, pharmaceutical compositions thereof, and methods of treatment using same. The present invention also relates to stable amorphous co-precipitates of vilazodone hydrochloride with pharmaceutically acceptable excipients, methods for the preparation thereof, pharmaceutical compositions thereof, and methods of treatment using same.

BACKGROUND OF THE INVENTION

U.S. Pat. No. 5,532,241 (hereinafter referred to as the '241 patent) discloses a variety of piperidine and piperazine derivatives and their pharmaceutically acceptable salts, processes for their preparation, pharmaceutical compositions comprising the derivatives, and methods of use thereof. These compounds are active on the central nervous system, especially in terms of $5\text{-HT}_{1A}$-agonist and 5-HT-reuptake inhibition. They are furthermore active as serotonin agonists and antagonists. These compounds and their physiologically acceptable acid addition salts can, therefore, be used as active ingredients for anxiolytics, antidepressants, antipsychotics, neuroleptics, and antihypertensives. Among them, Vilazodone hydrochloride, 5-[4-[4-(5-Cyanoindol-3-yl)butyl]piperazin-1-yl]benzofuran-2-carboxamide hydrochloride, is a serotonergic antidepressant that is used for the treatment of major depressive disorder (MDD). Vilazodone hydrochloride is represented by the following structural formula:

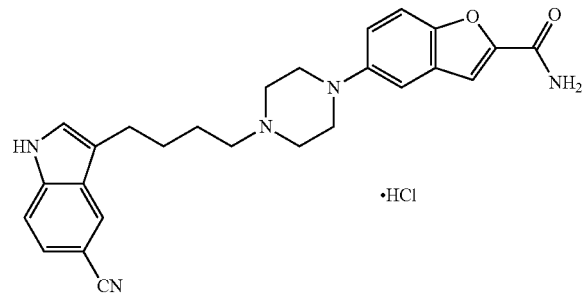 [SMILES: N#Cc1ccc2[nH]cc(CCCCN3CCN(c4ccc5oc(C(N)=O)cc5c4)CC3)c2c1 ; Cl]

Vilazodone was approved by the FDA for use in the United States to treat major depressive disorder and it is sold under the trade name VIIBRYD™. It is orally administered as tablets containing 10 mg, 20 mg and 40 mg of vilazodone as the hydrochloride salt.

PCT Publication No. WO02/102794A2 (hereinafter referred to as the '794 publication) discloses several crystalline modifications (Crystalline Forms I, II, III, IV, V, VI, VII, VIII, IX, X, XI, XIII, XIV, XV and XVI) of vilazodone hydrochloride, which include six anhydrate forms, three hydrated fowls and six solvated forms, wherein Form I is an acetone solvate; Forms II, XV and X are tetrahydrofuran solvates; Form XI is a methanol solvate; and Form XIV is an n-heptane solvate. Form V is monohydrate, Form VI is a sesquihydrate and Form VIII is a hemihydrate. Forms III, IV, VII and IX are anhydrate crystalline forms of vilazodone hydrochloride. Form XIII is a crystalline modification of vilazodone dihydrochloride. These crystalline modifications are characterized by powder X-ray diffraction (P-XRD), Infra Red spectroscopy (IR), RAMAN spectroscopy and thermal analysis.

The '794 publication teaches that the product (Vilazodone hydrochloride) obtained according to the process described in the prior art, for example, as per the process exemplified in example 4 of U.S. Pat. No. 5,532,241, followed by customary work-up to produce vilazodone free base and subsequent precipitation of vilazodone hydrochloride by treating the solution of the vilazodone base (700 mg) in 2-propanol (30 ml) with 2-propanolic HCl-solution (Merck-Art. No. 1.00326), is a mixture of amorphous vilazodone hydrochloride and crystallized vilazodone hydrochloride and the vilazodone free base.

A similar process for the precipitation of vilazodone hydrochloride is also reported in Journal of Medicinal Chemistry, 2004, Vol. 47, No. 19, pages 4684-4692 (hereinafter referred to as the 'JMC article'). As per the process reported in the JMC article (see column-1, lines 47-57 of Page No. 4690), the vilazodone hydrochloride is precipitated by dissolving vilazodone free base (0.7 g) in 30 ml of hot 2-propanol to form a solution, followed by slow addition of HCl-saturated 2-propanol at room temperature until complete precipitation occurred to yield 0.6 g of vilazodone hydrochloride (Melting Point: 277-279° C.).

The '794 publication further teaches that there is no clear teaching elsewhere in the '241 patent of any alternative route or modification to the process which would generate new crystal modifications of vilazodone hydrochloride or new solvates or hydrates of vilazodone hydrochloride in different crystal modifications.

The '794 publication further teaches an amorphous form of vilazodone hydrochloride. While the '794 publication mentions that a pure amorphous form of vilazodone hydrochloride has been found, there is no clear disclosure about amorphous form since the '794 publication neither disclosed the characterization data (X-ray diffractogram) nor described the process for the preparation of a pure amorphous form of vilazodone hydrochloride.

The processes described in the aforementioned prior art have failed to produce a pure amorphous form of vilazodone hydrochloride substantially free of crystalline forms. Instead, the prior art processes yield a solid state form containing the mixture of amorphous vilazodone hydrochloride and crystallized vilazodone hydrochloride and the vilazodone free base, which is not suitable for pharmaceutical use.

Polymorphism is the ability of a solid material to exist in more than one form or crystal structure. Amorphous solids consist of disordered arrangement of molecules and do not possess a distinguishable crystal lattice. The amorphous form is generally more soluble than the crystalline form and thus contributes more in the bioavailability.

An important solid state property of a pharmaceutical compound is its rate of dissolution in aqueous fluid. The rate of dissolution of an active ingredient in a patient's stomach fluid may have therapeutic consequences since it imposes an upper limit on the rate at which an orally-administered pharmaceutical compound may reach the patient's bloodstream. The rate of dissolution is a consideration in formulating syrups, elixirs and other liquid medicaments. The solid state form of a compound may also affect its behavior on compaction and its storage stability.

It has been disclosed in the art that the amorphous forms of a number of pharmaceutical compounds exhibit superior dissolution characteristics and in some cases different bioavailability patterns compared to crystalline forms [Konno T., Chem. Pharm. Bull., 38, 2003 (1990)]. For some therapeutic indications, one bioavailability pattern may be favored over another.

Solvent medium and mode of isolation play very important roles in obtaining one polymorphic form over another.

Amorphous form of vilazodone hydrochloride substantially free of crystalline forms has not been prepared, isolated, or characterized in the literature.

Hence, there is a need in the art for highly pure and stable amorphous form of vilazodone hydrochloride essentially free of crystalline forms, a process for its preparation and a pharmaceutical composition thereof.

SUMMARY OF THE INVENTION

We have now surprisingly and unexpectedly found an amorphous form of vilazodone hydrochloride substantially free of crystalline forms, having adequate stability and good dissolution properties, which is different from the material obtained according to the teachings of the '794 publication and as well as according to the method reported in the JMC article.

We have repeated the process for the isolation of vilazodone hydrochloride as reported in the JMC article. In our hands, the method reported in the JMC article yields a solid state form, which we denote as Form A, characterized by an X-ray powder diffraction pattern having peaks expressed as 2-theta angle positions at about 5.73, 8.79, 9.56, 10.07, 10.65, 11.05, 11.71, 13.73, 14.98, 17.64, 18.84, 20.49, 21.13, 22.05, 24.73, 25.47, 26.33, 27.48, 29.09, 30.28 and 31.60±0.2 degrees substantially in accordance with FIG. 16, which is different from the amorphous form of vilazodone hydrochloride substantially free of crystalline forms of the present invention.

The amorphous form of vilazodone hydrochloride substantially free of crystalline forms is consistently reproducible, does not have the tendency to convert to other forms, and is found to be more stable. The amorphous vilazodone hydrochloride essentially free of crystalline forms disclosed herein exhibits properties making it suitable for formulating vilazodone hydrochloride.

In one aspect, provided herein is a highly pure and stable amorphous form of vilazodone hydrochloride substantially free of crystalline forms.

In another aspect, provided herein is a highly pure and stable amorphous form of vilazodone hydrochloride essentially free of crystalline forms.

In another aspect, encompassed herein is a process for preparing the highly pure and stable amorphous form of vilazodone hydrochloride substantially free of crystalline forms.

In another aspect, provided herein is a pharmaceutical composition comprising amorphous vilazodone hydrochloride substantially free of crystalline forms as disclosed herein and one or more pharmaceutically acceptable excipients.

In still another aspect, provided herein is a pharmaceutical composition comprising amorphous vilazodone hydrochloride essentially free of crystalline forms made by the process disclosed herein, and one or more pharmaceutically acceptable excipients.

In still further aspect, encompassed herein is a process for preparing a pharmaceutical formulation comprising combining amorphous vilazodone hydrochloride essentially free of crystalline forms with one or more pharmaceutically acceptable excipients.

In another aspect, provided herein are amorphous co-precipitates of vilazodone hydrochloride with pharmaceutically acceptable excipients. More particularly, disclosed herein are amorphous co-precipitates of vilazodone hydrochloride with improved physiochemical characteristics which help in the effective bioavailability of vilazodone hydrochloride. Such pharmaceutical compositions may be administered easily to a mammalian patient in a dosage form, e.g., liquid, powder, elixir, injectable solution, with a high rate of bioavailability.

In yet another aspect, encompassed herein is a process for preparing the novel and stable amorphous co-precipitates of vilazodone hydrochloride with pharmaceutically acceptable excipients.

The amorphous co-precipitate of vilazodone hydrochloride obtained by the processes described herein has improved solubility properties and hence also has improved bioavailability.

In another aspect, provided herein are pharmaceutical compositions comprising the amorphous co-precipitates of vilazodone hydrochloride and one or more pharmaceutically acceptable excipients.

In still further aspect, encompassed herein is a process for preparing pharmaceutical formulations comprising combining the amorphous co-precipitates of vilazodone hydrochloride with one or more pharmaceutically acceptable excipients.

In another aspect, the amorphous vilazodone hydrochloride substantially free of crystalline forms, or a co-precipitate thereof, disclosed herein for use in the pharmaceutical compositions has a $D_{90}$ particle size of less than or equal to about 400 microns, specifically about 1 micron to about 300 microns, and most specifically about 10 microns to about 150 microns.

The term "highly pure" is meant having purity greater than about 99%, specifically greater than about 99.5%, and more specifically greater than about 99.9%, as measured by HPLC.

BRIEF DESCRIPTION OF THE DRAWINGS

FIG. 13 is a characteristic powder X-ray diffraction (XRPD) pattern of Amorphous Co-precipitate of Vilazodone Hydrochloride with Hydroxypropyl cellulose (1:15).

FIG. 14 is a characteristic powder X-ray diffraction (XRPD) pattern of Amorphous Co-precipitate of Vilazodone Hydrochloride with Hydroxypropyl cellulose (1:10)

FIG. 15 is a characteristic powder X-ray diffraction (XRPD) pattern of Amorphous Co-precipitate of Vilazodone Hydrochloride with Hydroxypropyl cellulose (1:2)

FIG. 16 is a characteristic powder X-ray diffraction (XRPD) pattern of solid state form of Vilazodone hydrochloride obtained according to the Reference Example.

DETAILED DESCRIPTION OF THE INVENTION

According to one aspect, there is provided a stable and highly pure amorphous form of vilazodone hydrochloride substantially free of crystalline forms.

According to another aspect, there is provided a stable and highly pure amorphous form of vilazodone hydrochloride essentially free of crystalline forms.

The term "amorphous" means a solid without long-range crystalline order. The term "amorphous form of vilazodone hydrochloride substantially free of crystalline forms" means that the amorphous form of vilazodone hydrochloride that contains less than about 5 percent crystalline forms of vilazodone hydrochloride, specifically less than 1 percent crystalline forms of vilazodone hydrochloride, and more specifically is essentially free of crystalline forms of vilazodone hydrochloride.

"Essentially free of crystalline forms of vilazodone hydrochloride" means that no crystalline polymorph forms of vilazodone hydrochloride can be detected within the limits of a powder X-ray diffractometer.

The amorphous form of vilazodone hydrochloride substantially free of crystalline forms is characterized by a powder XRD pattern substantially in accordance with FIG. 1, FIG. 3, FIG. 5 or FIG. 6.

Figure 1:
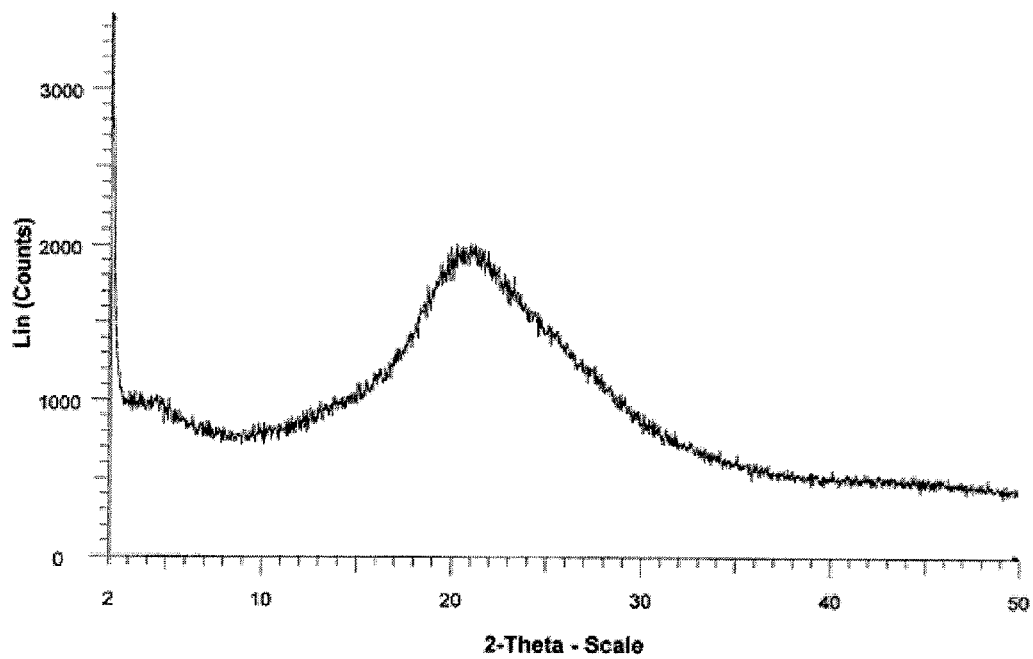
FIG. 1 is a characteristic powder X-ray diffraction (XRPD) pattern of amorphous form of Vilazodone hydrochloride obtained according to the Example 1.
Figure 3:
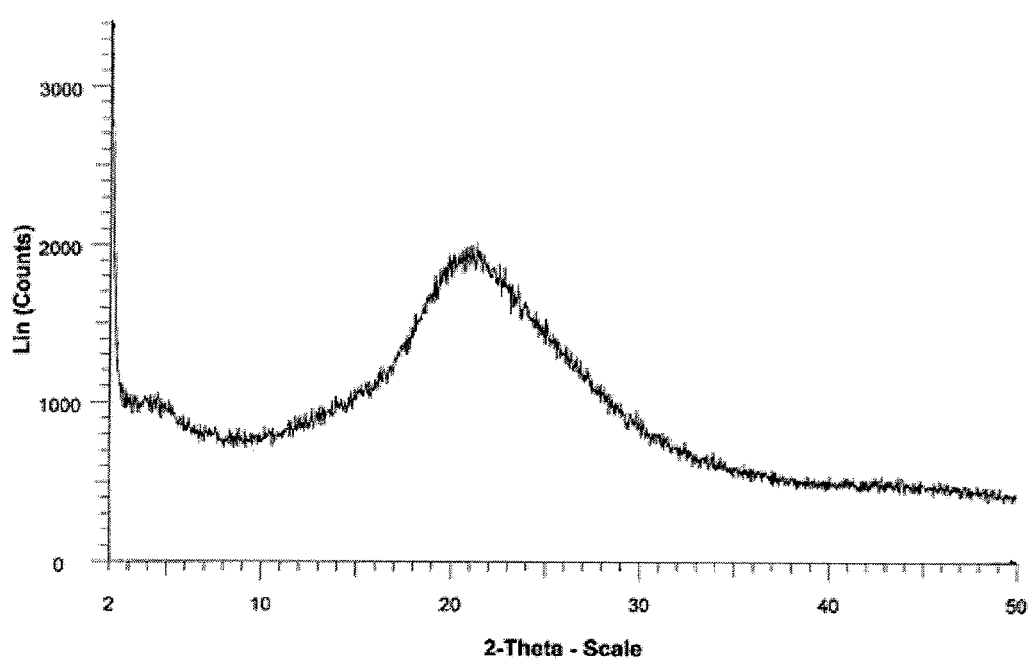
FIG. 3 is a characteristic powder X-ray diffraction (XRPD) pattern of amorphous form of Vilazodone hydrochloride obtained according to the Example 2.

In one embodiment, the amorphous form of vilazodone hydrochloride essentially free of crystalline forms is characterized by a powder XRD pattern substantially in accordance with FIG. 1 or FIG. 3. The X-ray powder diffraction pattern shows a plain halo with no well-defined peaks, thus demonstrating the amorphous nature of the product.

Figure 2:
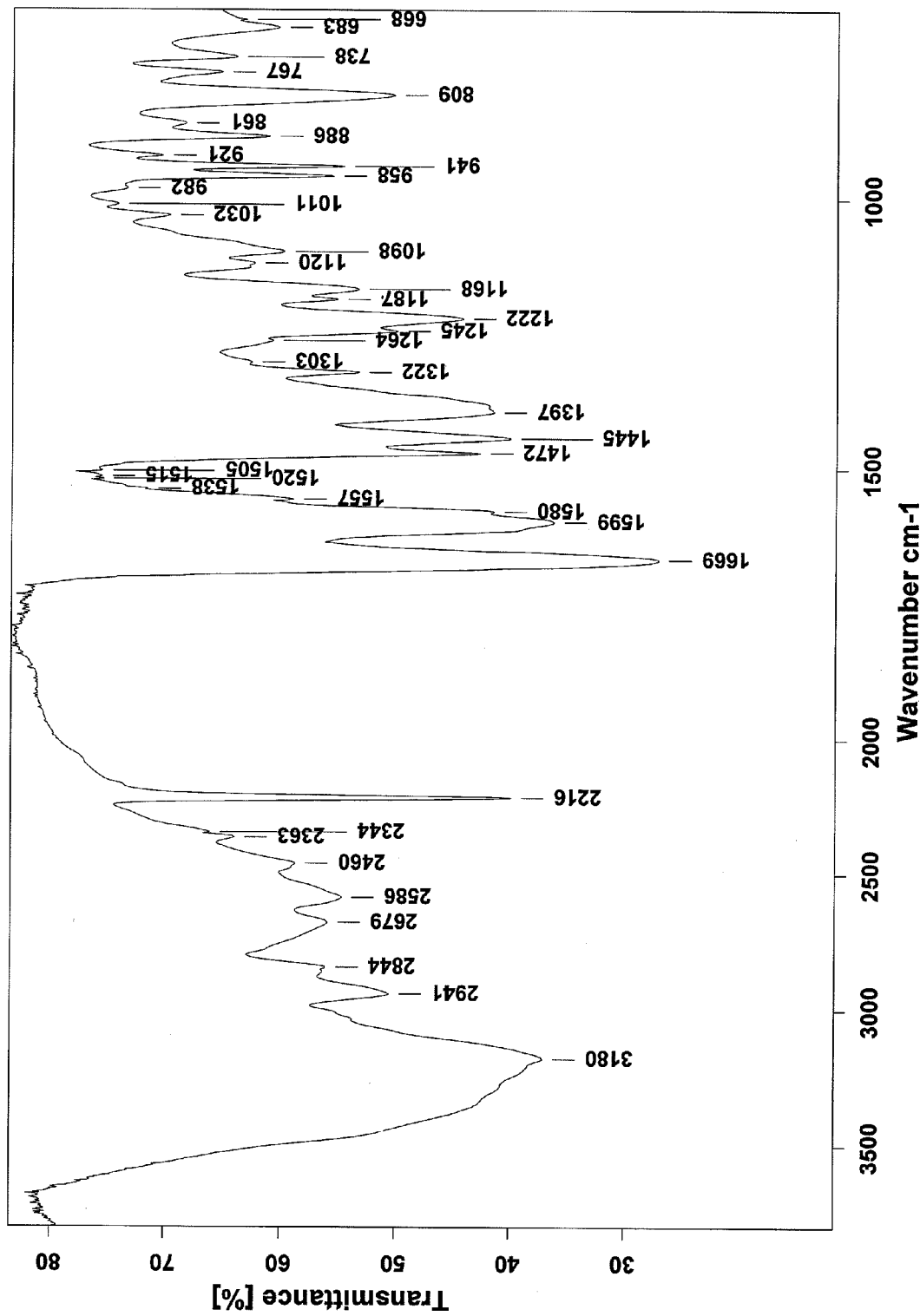
FIG. 2 is a characteristic infra red (IR) spectrum of amorphous form of Vilazodone hydrochloride obtained according to the Example 1.
Figure 4:
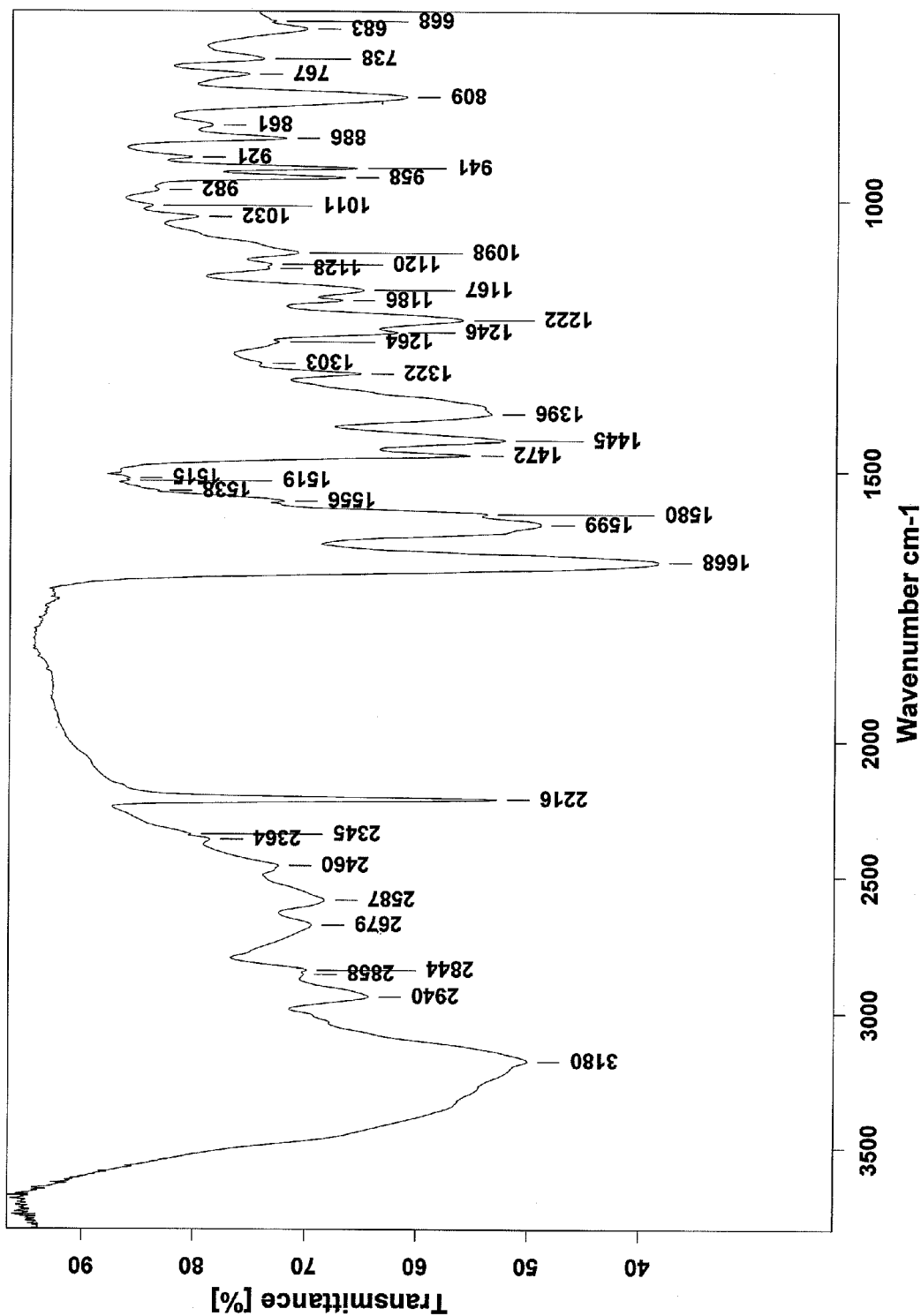
FIG. 4 is a characteristic infra red (IR) spectrum of amorphous form of Vilazodone hydrochloride obtained according to the Example 2.
Figure 5:
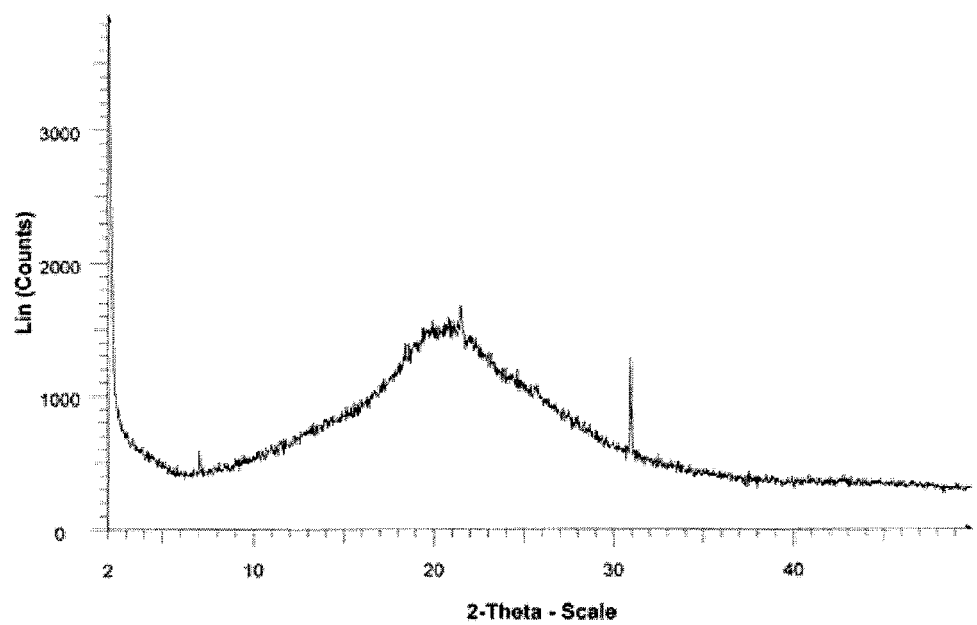
FIG. 5 is a characteristic powder X-ray diffraction (XRPD) pattern of amorphous form of Vilazodone hydrochloride obtained according to the Example 4.
Figure 6:
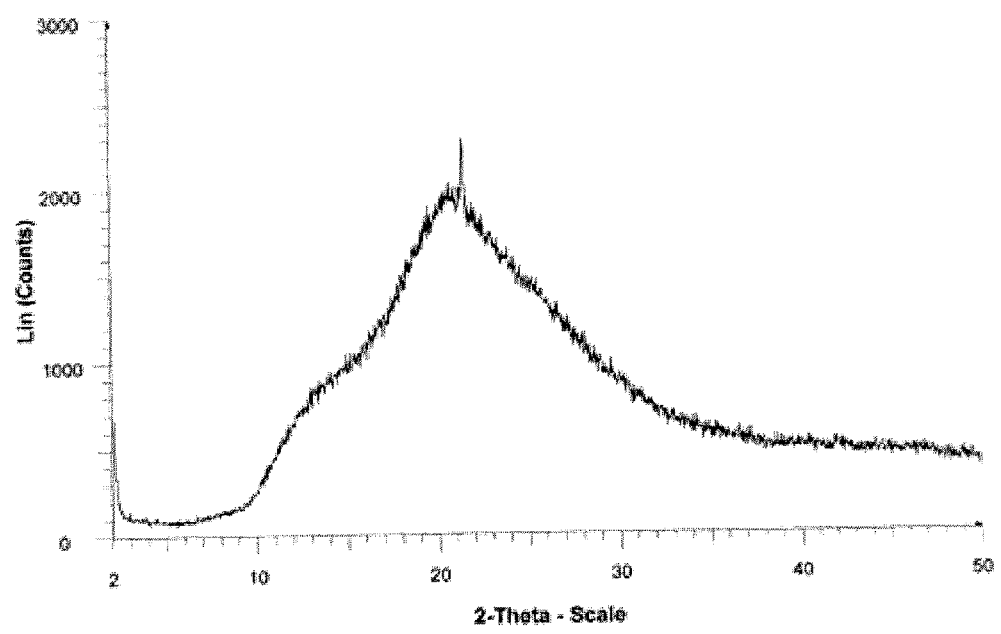
FIG. 6 is a characteristic powder X-ray diffraction (XRPD) pattern of amorphous form of Vilazodone hydrochloride obtained according to the Example 5.

The amorphous form of vilazodone hydrochloride essentially free of crystalline forms is further characterized by an infra red (FT-IR) spectrum having main bands at about 3180, 2940, 2844, 2679, 2587, 2460, 2345, 2216, 1668, 1599, 1580, 1472, 1445, 1396, 1322, 1246, 1222, 1167, 1098, 958, 941, 886, 809, 738, 683 and 668+2 $cm^{-1}$ substantially in accordance with FIG. 2 or FIG. 4.

According to another aspect, there is provided a process for the preparation of an amorphous form of vilazodone hydrochloride substantially free of crystalline forms, comprising:

a) providing a solution of vilazodone hydrochloride in a solvent selected from the group consisting of water, an alcohol, and mixtures thereof;

b) optionally, subjecting the solution obtained in step-(a) to carbon treatment or silica gel treatment to obtain a filtrate;

c) cooling the solution obtained in step-(a) or step-(b) to room temperature; and d) removing the solvent from the solution obtained in step-(c) by subjecting the solution to spray drying to produce the highly pure amorphous form of vilazodone hydrochloride substantially or essentially free of crystalline forms.

The amorphous form of vilazodone hydrochloride substantially free of crystalline forms obtained by the process disclosed herein is stable, consistently reproducible, has good dissolution and flow properties, and is particularly suitable for bulk preparation and handling.

In one embodiment, the process disclosed herein provides stable amorphous form of vilazodone hydrochloride. The term "stable amorphous form" refers to stability of the amorphous form under the standard temperature and humidity conditions of testing of pharmaceutical products, wherein the stability is indicated by preservation of the original solid state form.

The amorphous form of vilazodone hydrochloride substantially free of crystalline forms obtained by the process disclosed herein is suitable for formulating vilazodone hydrochloride.

As used herein, room temperature is meant to indicate a temperature of about 25° C. to about 35° C., preferably about 25° C. to about 30° C.

Exemplary alcohol solvents used in step-(a) include, but are not limited to, methanol, ethanol, n-propanol, isopropyl alcohol, isobutanol, n-butanol, tert-butanol, and mixtures thereof.

A most specific alcohol solvent used in step-(a) is methanol.

Step-(a) of providing a solution of vilazodone hydrochloride includes dissolving vilazodone hydrochloride in the solvent, or obtaining an existing solution from a previous processing step.

In one embodiment, the vilazodone hydrochloride is dissolved in the solvent at a temperature of about 25° C. to about the reflux temperature of the solvent used, specifically at about 50° C. to about 90° C., and most specifically at about 55° C. to about 65° C.

As used herein, "reflux temperature" means the temperature at which the solvent or solvent system refluxes or boils at atmospheric pressure.

In another embodiment, the solution in step-(a) is prepared by admixing vilazodone base, hydrochloric acid and the solvent to obtain a mixture, and stirring the mixture at a temperature of above about 40° C. In yet another embodiment, the mixture is stirred at a temperature of about 40° C. to about 100° C. for about 10 minutes to about 2 hours, and still more specifically at about 55° C. to about 65° C. for about 15 minutes to about 30 minutes.

Hydrochloric acid used may be in the form of aqueous hydrochloric acid, in the form of hydrogen chloride gas, or as hydrogen chloride dissolved in an alcohol solvent, specifically methanol.

The carbon treatment or silica gel treatment in step-(b) is carried out by methods known in the art, for example by stirring the solution with finely powdered carbon or silica gel at a temperature of below about 70° C. for at least 5 minutes, specifically at a temperature of about 40° C. to about 70° C. for at least 30 minutes; and filtering the resulting mixture through hyflo bed to obtain a filtrate containing vilazodone hydrochloride by removing charcoal or silica gel. Preferably, a finely powdered carbon is an active carbon. In one embodiment, a specific mesh size of silica gel is 40-500 mesh, and more specifically 60-120 mesh.

The solution obtained in step-(a) or step-(b) may optionally be seeded with amorphous form of vilazodone hydrochloride.

In one embodiment, the solution in step-(c) is cooled to a temperature of about 25° C. to about 30° C.

Specifically, the removal of solvent in step-(d) is accomplished by spray-drying, in which a solution of vilazodone hydrochloride is sprayed into the spray drier. The air inlet temperature to the spray drier used may range from about 65° C. to about 125° C., specifically from about 70° C. to about 110° C. and most specifically from about 70° C. to about 105° C.; and the outlet air temperature used may range from about 30° C. to about 70° C., and specifically from about 35° C. to about 65° C.

The term "spray drying" broadly refers to processes involving breaking up liquid mixtures into small droplets (atomization) and rapidly removing solvent from the mixture. In a typical spray drying apparatus, a strong driving force evaporates the solvent from the droplets, which may be provided by providing a drying gas. Spray drying processes and equipment are described in Perry's Chemical Engineer's Handbook, pages. 20-54 to 20-57 (Sixth Edition 1984). By way of non-limiting example only, the typical spray drying apparatus comprises a drying chamber, atomizing means for atomizing a solvent-containing feed into the drying chamber, a source of drying gas that flows into the drying chamber to remove solvent from the atomized-solvent-containing feed, an outlet for the products of drying, and product collection means located downstream from the drying chamber. Typically, the product collection means includes a cyclone connected to the drying apparatus. In the cyclone, the particles produced during spray drying are separated from the drying gas and evaporated solvent, allowing the particles to be collected. A filter may also be used to separate and collect the particles produced by spray drying.

Spray drying may be performed in a conventional manner in the processes of the present invention. The drying gas used in the invention may be any suitable gas, although inert gases such as nitrogen, nitrogen-enriched air; and argon are preferred. Nitrogen gas is a particularly preferred drying gas for use in the process of the invention. The vilazodone hydrochloride product produced by spray drying may be recovered by techniques commonly used in the art, such as using a cyclone or a filter.

Removal of solvent in step-(d) may also be accomplished, for example, by substantially complete evaporation of the solvent, concentrating the solution, or distillation of solvent, under inert atmosphere to obtain amorphous vilazodone hydrochloride.

According to another aspect, there is provided a process for the preparation of an amorphous form of vilazodone hydrochloride substantially free of crystalline forms, comprising:
a) providing a solution of vilazodone hydrochloride in methanol;
b) optionally, subjecting the solution obtained in step-(a) to carbon treatment or silica gel treatment to obtain a filtrate;
c) cooling the solution obtained in step-(a) or step-(b) to room temperature; and
d) removing the solvent from the solution obtained in step-(c) by subjecting the solution to spray drying to produce the highly pure amorphous form of vilazodone hydrochloride substantially or essentially free of crystalline forms, wherein the air inlet temperature to the spray drier ranges from about 70° C. to about 110° C., and the outlet air temperature ranges from about 30° C. to about 70° C.

The pure amorphous vilazodone hydrochloride obtained by the above process may optionally be further dried in, for example, a Vacuum Tray Dryer, a Rotocon Vacuum Dryer, a Vacuum Paddle Dryer or a pilot plant Rota vapor, to further lower residual solvents. Drying can be carried out under reduced pressure until the residual solvent content reduces to the desired amount such as an amount that is within the limits given by the International Conference on Harmonization of Technical Requirements for Registration of Pharmaceuticals for Human Use ("ICH") guidelines.

In one embodiment, the drying is carried out at atmospheric pressure or reduced pressures, such as below about 200 mm Hg, or below about 50 mm Hg, at temperatures such as about 25° C. to about 90° C. The drying can be carried out for any desired time period that achieves the desired result, such as times about 1 to 20 hours. Drying may also be carried out for shorter or longer periods of time depending on the product specifications. Temperatures and pressures will be chosen based on the volatility of the solvent being used and the foregoing conditions should be considered as only a general guidance. Drying can be suitably carried out in a tray dryer, vacuum oven, air oven, or using a fluidized bed drier, spin flash dryer, flash dryer, and the like. Drying equipment selection is well within the ordinary skill in the art.

The purity of the amorphous form of vilazodone hydrochloride substantially free of crystalline forms obtained by the process disclosed herein is greater than about 99%, specifically greater than about 99.5%, more specifically greater than about 99.9%, and most specifically greater than about 99.95% as measured by HPLC. For example, the purity of the amorphous form of vilazodone hydrochloride essentially free of crystalline forms can be about 99% to about 99.95, or about 99.5% to about 99.99%.

Vilazodone hydrochloride or its free base as used herein as starting materials can be obtained by the processes described in the prior art, for example, the process described in the U.S. Pat. No. 5,532,241 or the JMC Article.

According to another aspect, there are provided amorphous co-precipitates comprising vilazodone hydrochloride and a pharmaceutically acceptable excipient, having improved physiochemical characteristics that assist in the effective bioavailability of vilazodone hydrochloride.

In one embodiment, the pharmaceutically acceptable excipient is selected from the group consisting of polyvinylpyrrolidone (also called povidone or PVP), polyvinyl alcohol, hydroxypropyl cellulose (HPC), hydroxypropyl methylcellulose (HPMC), methyl cellulose, carboxymethyl cellulose, sodium carboxymethyl cellulose, hydroxyethylcellulose, hypromellose phthalate (HPMCP), lactose monohydrate, polyvinyl acetate, maltodextrins, cyclodextrins, gelatins, sugars, and combinations comprising one or more of the foregoing hydrophilic carriers.

Specific pharmaceutically acceptable excipients are polyvinylpyrrolidone, maltodextrin, lactose monohydrate, hydroxypropyl cellulose, hydroxypropyl methylcellulose and hypromellose phthalate.

According to another aspect, there are provided pharmaceutical compositions comprising amorphous co-precipitates of vilazodone hydrochloride, and one or more pharmaceutically acceptable excipients.

The amorphous co-precipitates of vilazodone hydrochloride with a pharmaceutically acceptable carrier obtained by the processes disclosed herein may be characterized by one or more of their powder X-ray diffraction (XRD) pattern, infrared absorption (IR) spectrum, and SEM images of the morphological analysis.

Figure 7:
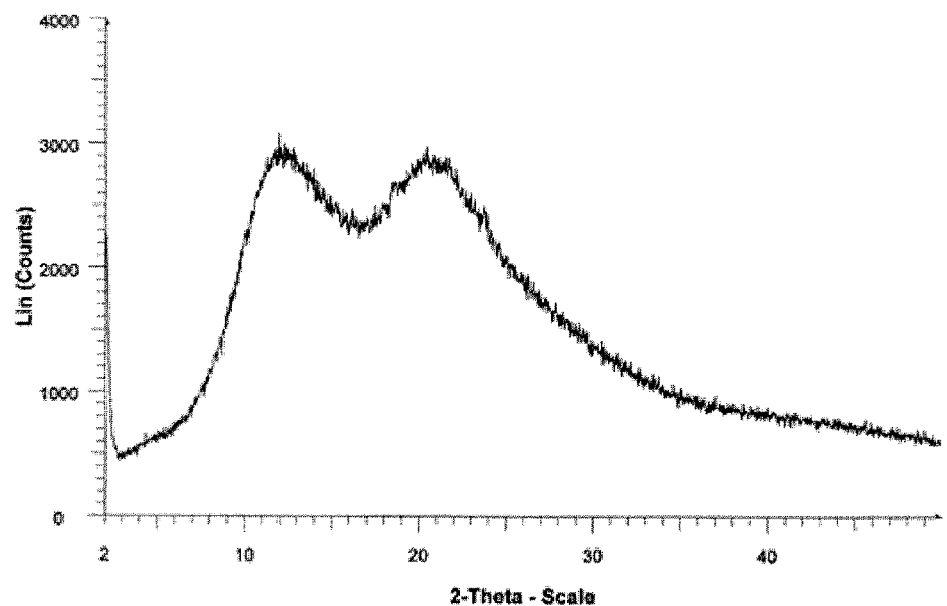
FIG. 7 is a characteristic powder X-ray diffraction (XRPD) pattern of Amorphous Co-precipitate of Vilazodone Hydrochloride with Polyvinylpyrrolidone (1:10).

In one embodiment, the amorphous co-precipitate of vilazodone hydrochloride with polyvinylpyrrolidone (1:10) is characterized by a powder XRD pattern substantially in accordance with FIG. 7. The X-ray powder diffraction pattern shows a plain halo with no well-defined peaks, thus demonstrating the amorphous nature of the product.

Figure 8:
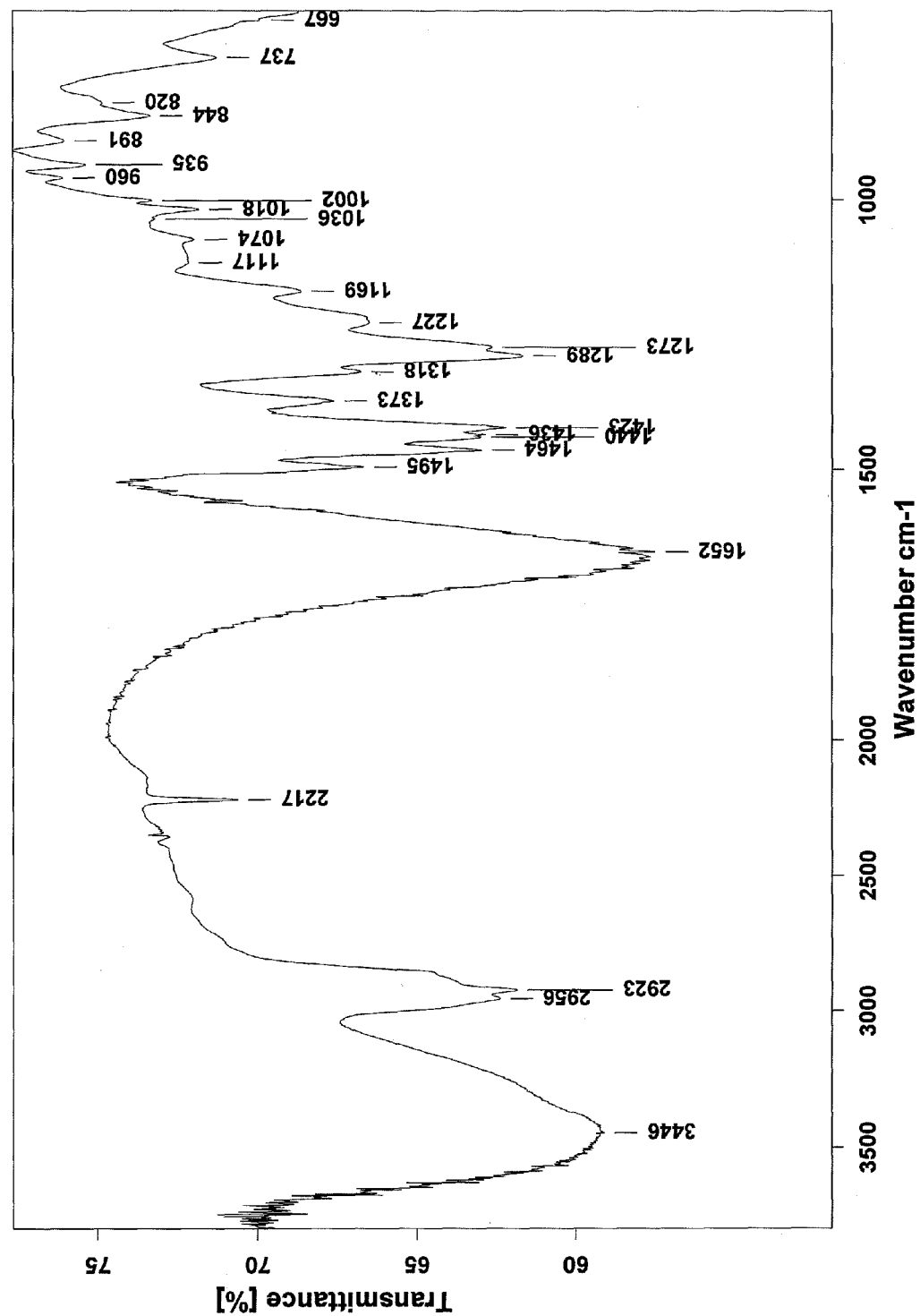
FIG. 8 is a characteristic infra red (IR) spectrum of amorphous form of Amorphous Co-precipitate of Vilazodone Hydrochloride with Polyvinylpyrrolidone (1:10).

The amorphous co-precipitate of vilazodone hydrochloride with polyvinylpyrrolidone (1:10) is further characterized by an infra red (FT-IR) spectrum having main bands at about 3446, 2956, 2923, 2217, 1652, 1495, 1464, 1440, 1423, 1373, 1318, 1289, 1273, 1227, 1169, 1074, 1018, 960, 935, 891, 844, 820 and 737±2 cm$^{-1}$ substantially in accordance with FIG. 8.

Figure 9:
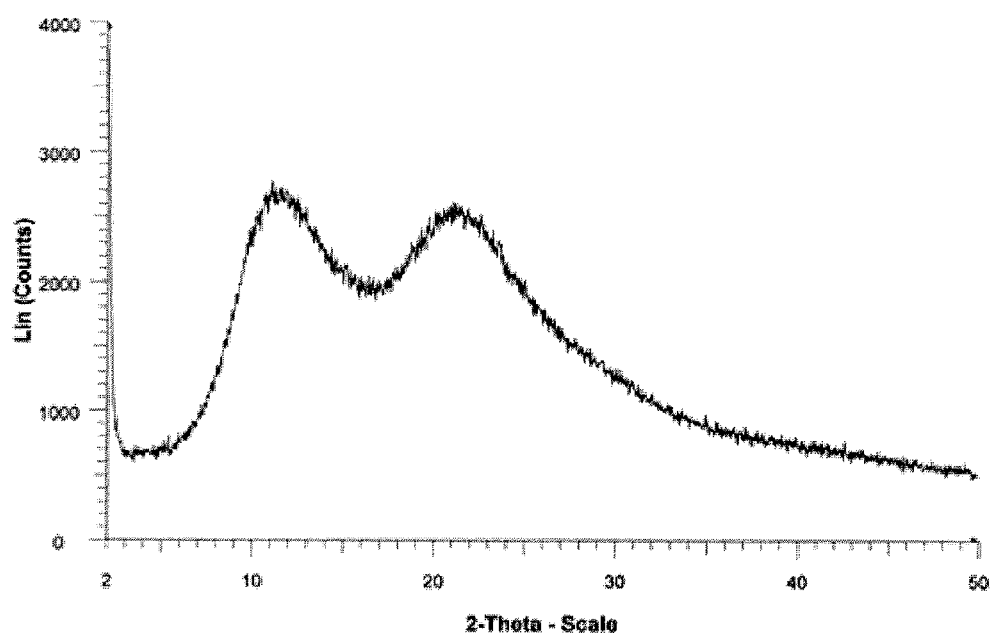
FIG. 9 is a characteristic powder X-ray diffraction (XRPD) pattern of Amorphous Co-precipitate of Vilazodone Hydrochloride with Polyvinylpyrrolidone (1:5).

In another embodiment, the amorphous co-precipitate of vilazodone hydrochloride with polyvinylpyrrolidone (1:5) is characterized by a powder XRD pattern substantially in accordance with FIG. 9. The X-ray powder diffraction pattern shows a plain halo with no well-defined peaks, thus demonstrating the amorphous nature of the product.

Figure 10:
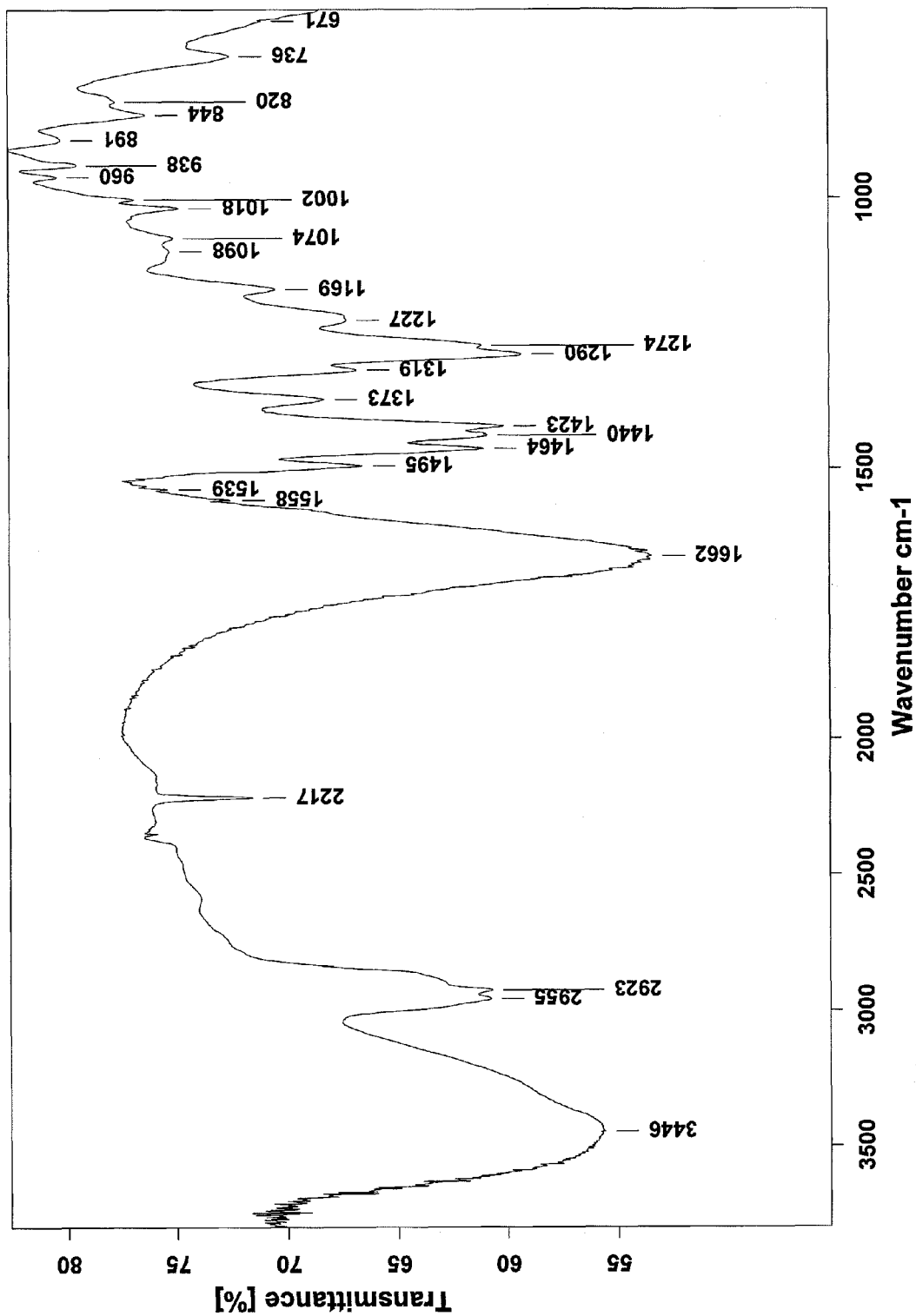
FIG. 10 is a characteristic infra red (IR) spectrum of amorphous form of Amorphous Co-precipitate of Vilazodone Hydrochloride with Polyvinylpyrrolidone (1:5).

The amorphous co-precipitate of vilazodone hydrochloride with polyvinylpyrrolidone (1:5) is further characterized by an infra red (FT-IR) spectrum having main bands at about 3446, 2955, 2923, 2217, 1662, 1495, 1464, 1440, 1423, 1373, 1319, 1290, 1274, 1227, 1169, 1074, 1018, 960, 938, 891, 844, 820 and 736±2 cm$^{-1}$ substantially in accordance with FIG. 10.

Figure 11:
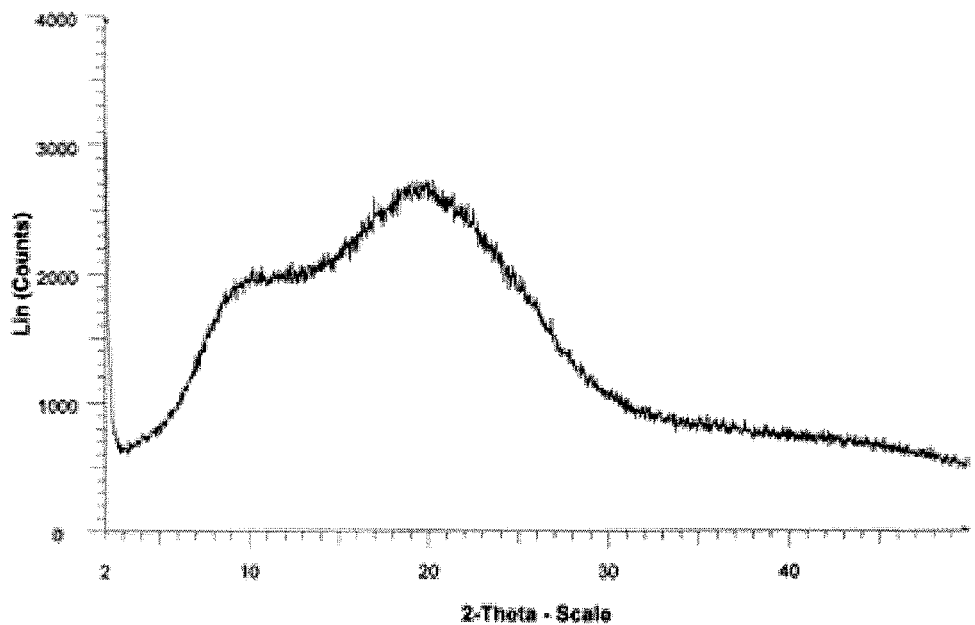
FIG. 11 is a characteristic powder X-ray diffraction (XRPD) pattern of Amorphous Co-precipitate of Vilazodone Hydrochloride with Hypromellose phthalate (1:10).

In another embodiment, the amorphous co-precipitate of vilazodone hydrochloride with hypromellose phthalate (1:10) is characterized by a powder XRD pattern substantially in accordance with FIG. 11. The X-ray powder diffraction pattern shows a plain halo with no well-defined peaks, thus demonstrating the amorphous nature of the product.

Figure 12:
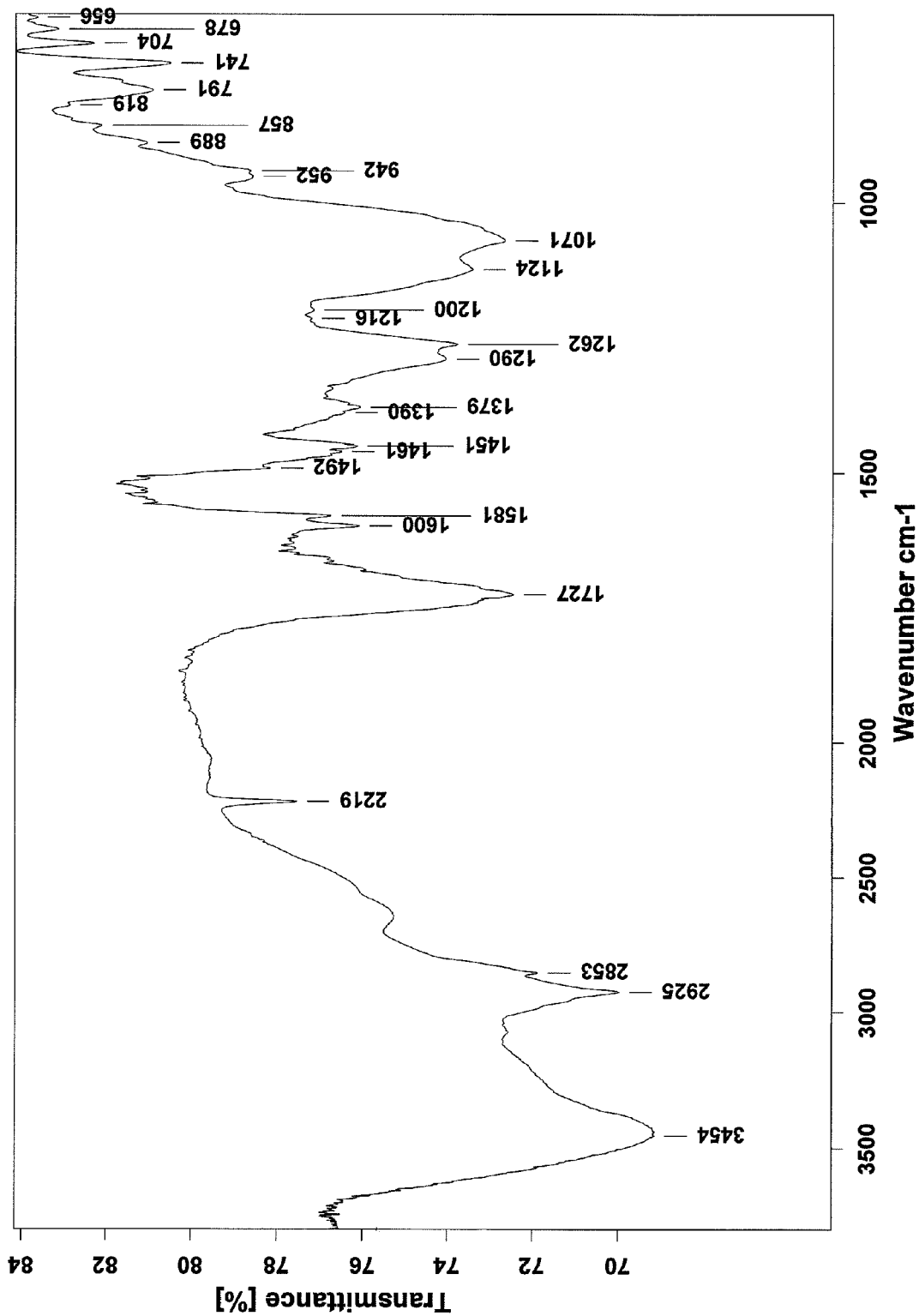
FIG. 12 is a characteristic infra red (IR) spectrum of amorphous form of Amorphous Co-precipitate of Vilazodone Hydrochloride with Hypromellose phthalate (1:10).

The amorphous co-precipitate of vilazodone hydrochloride with hypromellose phthalate (1:10) is further characterized by an infra red (FT-IR) spectrum having main bands at about 3454, 2925, 2853, 2219, 1727, 1600, 1581, 1492, 1461, 1451, 1379, 1290, 1262, 1216, 1124, 1071, 952, 942, 889, 857, 819 and 741+2 cm$^{-1}$ substantially in accordance with FIG. 12.

In another embodiment, the amorphous co-precipitate of vilazodone hydrochloride with hydroxypropyl cellulose is characterized by a powder XRD pattern, showing no well-defined peaks, substantially in accordance with FIG. 13, FIG. 14 or FIG. 15.

According to another aspect, there is provided a process for preparing an amorphous co-precipitate of vilazodone hydrochloride and a pharmaceutically acceptable excipient, comprising:

a) providing a solution of vilazodone hydrochloride and a pharmaceutically acceptable excipient in a solvent selected from the group consisting of water, an alcohol, an ester, a polar aprotic solvent, and mixtures thereof;
b) optionally, filtering the solvent solution to remove insoluble matter; and
c) substantially removing the solvent from the solution to produce the amorphous co-precipitate of vilazodone hydrochloride with the pharmaceutically acceptable excipient.

The process can produce amorphous co-precipitates of vilazodone hydrochloride with a pharmaceutically acceptable excipient in substantially pure form.

The amorphous co-precipitates of vilazodone hydrochloride obtained by the process disclosed herein are stable, consistently reproducible and have good flow properties, and which is particularly suitable for bulk preparation and handling. The novel co-precipitates obtained by the process disclosed herein are suitable for formulating vilazodone hydrochloride.

In one embodiment, the pharmaceutically acceptable excipient used in step-(a) is selected from the group as described above. Specific pharmaceutically acceptable excipients are polyvinylpyrrolidone, maltodextrin, lactose monohydrate, hydroxypropyl cellulose, hydroxypropyl methylcellulose and hypromellose phthalate. The use of mixtures of more than one of the pharmaceutical carriers to provide desired release profiles or for the enhancement of stability is within the scope of this invention. Also, all viscosity grades, molecular weights, commercially available products, their copolymers, mixtures are all within the scope of this invention without limitation.

In one embodiment, the povidone may be chosen from one or more of the grades such as PVP K-15, K-25, K-30, K29/32, K-60 and K-90.

In one embodiment, the solvent used in step-(a) is selected from the group consisting of water, methanol, ethanol, n-propanol, isopropyl alcohol, isobutanol, n-butanol, tert-butanol, ethyl acetate, methyl acetate, isopropyl acetate, tert-butyl methyl acetate, ethyl formate, N,N-dimethylformamide, N,N-dimethylacetamide, dimethylsulfoxide, and mixtures thereof.

Specifically, the solvent used in step-(a) is selected from the group consisting of water, methanol, ethanol, isopropyl alcohol, and mixtures thereof; and a most specific solvent is methanol.

Step-(a) of providing a solution of vilazodone hydrochloride includes dissolving vilazodone hydrochloride in the solvent, or such a solution may be obtained directly from a reaction in which vilazodone hydrochloride is formed. The pharmaceutical excipient can be dissolved in a solution containing vilazodone hydrochloride, or, vilazodone hydrochloride can be dissolved in a solution containing a pharmaceutical excipient.

Alternatively, a solution containing vilazodone hydrochloride can be combined with a solution containing a pharmaceutically acceptable excipient, and the solvents used for preparing the different solutions need not be the same as long as the solvents have mutual solubility and form a single phase. In any event, vilazodone hydrochloride should be completely soluble in the solvents used and should provide a clear solution. The presence of undissolved crystals could lead to the formation of a material that is not completely amorphous.

In one embodiment, the dissolution is carried out at a temperature of about 20° C. to about 140° C., specifically at about 25° C. to about 100° C., and more specifically at about 30° C. to about 80° C.

In another embodiment, the solution obtained in step-(a) is optionally be subjected to carbon treatment or silica gel treatment according to the methods described herein above.

The solution obtained in step-(a) is optionally stirred at a temperature of about 30° C. to the reflux temperature of the solvent used for at least 10 minutes, and specifically at a temperature of about 40° C. to the reflux temperature of the solvent used for about 20 minutes to about 4 hours.

Removal of solvent in step-(c) may also be accomplished, for example, by substantially complete evaporation of the solvent, concentrating the solution, or distillation of solvent, under inert atmosphere to obtain amorphous vilazodone hydrochloride.

Specifically, the removal of solvent in step-(c) is carried out by distillation. The distillation process can be performed at atmospheric pressure or at reduced pressure.

In one embodiment, the solvent is removed at a pressure of about 760 mm Hg or less, specifically at about 400 mm Hg or less, more specifically at about 80 mm Hg or less, and most specifically from about 30 to about 80 mm Hg.

In a preferred embodiment, the distillation process is performed under reduced pressure and at a temperature of about 50° C. to about 110° C., and most specifically at a temperature of about 60° C. to about 80° C.

In another embodiment, the solvent is removed by evaporation. Evaporation can be achieved at sub-zero temperatures by lyophilisation or freeze-drying techniques. The solution may also be completely evaporated in, for example, a pilot plant Rota vapor, a Vacuum Paddle Dryer or in a conventional reactor under vacuum above about 720 mm Hg by flash evaporation techniques by using an agitated thin film dryer ("ATFD").

In another embodiment, the removal of solvent in step-(c) is accomplished by spray-drying. The air inlet temperature to the spray drier used may range from about 50° C. to about 150° C., specifically from about 60° C. to about 120° C. and most specifically from about 70° C. to about 100° C.; and the outlet air temperature used may range from about 30° C. to about 90° C.

Another suitable method is vertical agitated thin-film drying (or evaporation). Agitated thin film evaporation technology involves separating the volatile component using indirect heat transfer coupled with mechanical agitation of the flowing film under controlled conditions. In vertical agitated thin-film drying (or evaporation) (ATFD-V), the starting solution is fed from the top into a cylindrical space between a centered rotary agitator and an outside heating jacket. The rotor rotation agitates the downside-flowing solution while the heating jacket heats it.

The dried product obtained by the process disclosed herein above can optionally be milled to get desired particle sizes. Milling or micronization can be performed prior to drying, or after the completion of drying of the product. The milling operation reduces the size of particles and increases surface area of particles. Drying is more efficient when the particle size of the material is smaller and the surface area is higher, hence milling will frequently be performed prior to the drying operation.

Milling can be done suitably using jet milling equipment like an air jet mill, or using other conventional milling equipment.

The resulting amorphous powder compositions disclosed herein have improved solubility properties and hence also have improved bioavailability.

The amorphous co-precipitates of vilazodone hydrochloride with the pharmaceutically acceptable excipients obtained by the process disclosed herein are a random distribution of the vilazodone hydrochloride and the pharmaceutically acceptable excipient in a particle matrix. Without being held to any particular theory, the co-precipitates have the characteristics of solid dispersions at a molecular level, being in the nature of solid solutions. The solid solutions, or molecular dispersions, provide homogeneous particles in which substantially no discrete areas of only amorphous vilazodone hydrochloride and/or only pharmaceutically acceptable excipient can be observed.

Further encompassed herein is the use of the amorphous form of vilazodone hydrochloride substantially free of crystalline forms for the manufacture of a pharmaceutical composition together with a pharmaceutically acceptable carrier.

A specific pharmaceutical composition of the amorphous vilazodone hydrochloride is selected from a solid dosage form and an oral suspension.

In one embodiment, the amorphous form of vilazodone hydrochloride substantially free of crystalline forms, or a co-precipitate thereof, has a $D_{90}$ particle size of less than or equal to about 400 microns, specifically about 1 micron to about 300 microns, and most specifically about 10 microns to about 150 microns.

In another embodiment, the substantially pure amorphous form of vilazodone hydrochloride essentially free of crystalline forms, or a co-precipitate thereof, disclosed herein for use in the pharmaceutical compositions has a $D_{90}$ particle size of less than or equal to about 400 microns, specifically about 1 micron to about 300 microns, and most specifically about 10 microns to about 150 microns.

In another embodiment, the particle sizes of the amorphous form of vilazodone hydrochloride substantially free of crystalline forms, or a co-precipitate thereof, can be achieved by a mechanical process of reducing the size of particles which includes any one or more of cutting, chipping, crushing, milling, grinding, micronizing, trituration or other particle size reduction methods known in the art, to bring the solid state form to the desired particle size range.

According to another aspect, there is provided a method for treating a patient suffering from depressive disorders, anxiety disorders, bipolar disorders, mania, dementia, substance-related disorders, sexual dysfunctions, eating disorders, obesity, fibromyalgia, sleeping disorders, psychiatric disorders, cerebral infarct, tension, for the therapy of side-effects in the treatment of hypertension, cerebral disorders, chronic pain, acromegaly, hypogonadism, secondary amenorrhea, premenstrual syndrome and undesired puerperal lactation; comprising administering a therapeutically effective amount of the amorphous vilazodone hydrochloride essentially free of crystalline forms or a co-precipitate thereof, or a pharmaceutical composition that comprises a therapeutically effective amount of amorphous vilazodone hydrochloride essentially free of crystalline forms or a co-precipitate thereof along with pharmaceutically acceptable excipients.

According to another aspect, there are provided pharmaceutical compositions comprising amorphous vilazodone hydrochloride essentially free of crystalline forms, or a co-precipitate thereof, prepared according to the processes disclosed herein and one or more pharmaceutically acceptable excipients.

According to another aspect, there is provided a process for preparing a pharmaceutical formulation comprising combining amorphous vilazodone hydrochloride essentially free of crystalline forms, or a co-precipitate thereof, prepared according to processes disclosed herein, with one or more pharmaceutically acceptable excipients.

Yet in another embodiment, pharmaceutical compositions comprise at least a therapeutically effective amount of amorphous vilazodone hydrochloride essentially free of crystalline forms or a co-precipitate thereof. Such pharmaceutical compositions may be administered to a mammalian patient in a dosage form, e.g., solid, liquid, powder, elixir, aerosol, syrups, injectable solution, etc. Dosage forms may be adapted for administration to the patient by oral, buccal, parenteral, ophthalmic, rectal and transdermal routes or any other acceptable route of administration. Oral dosage forms include, but are not limited to, tablets, pills, capsules, syrup, troches, sachets, suspensions, powders, lozenges, elixirs and the like. The amorphous vilazodone hydrochloride essentially free of crystalline forms or a co-precipitate thereof may also be administered as suppositories, ophthalmic ointments and suspensions, and parenteral suspensions, which are administered by other routes.

The pharmaceutical compositions further contain one or more pharmaceutically acceptable excipients. Suitable excipients and the amounts to use may be readily determined by the formulation scientist based upon experience and consideration of standard procedures and reference works in the field, e.g., the buffering agents, sweetening agents, binders, diluents, fillers, lubricants, wetting agents and disintegrants described hereinabove.

In one embodiment, capsule dosage forms contain amorphous vilazodone hydrochloride essentially free of crystalline forms or a co-precipitate thereof within a capsule which may be coated with gelatin. Tablets and powders may also be coated with an enteric coating. Suitable enteric coating agents include phthalic acid cellulose acetate, hydroxypropylmethyl cellulose phthalate, polyvinyl alcohol phthalate, carboxy methyl ethyl cellulose, a copolymer of styrene and maleic acid, a copolymer of methacrylic acid and methyl methacrylate, and like materials, and if desired, the coating agents may be employed with suitable plasticizers and/or extending agents. A coated capsule or tablet may have a coating on the surface thereof or may be a capsule or tablet comprising a powder or granules with an enteric-coating.

Tableting compositions may have few or many components depending upon the tableting method used, the release rate desired and other factors. For example, the compositions described herein may contain diluents such as cellulose-derived materials like powdered cellulose, microcrystalline cellulose, micro fine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents such calcium carbonate and calcium diphosphate and other diluents known to one of ordinary skill in the art. Yet other suitable diluents include waxes, sugars (e.g. lactose) and sugar alcohols such as mannitol and sorbitol, acrylate polymers and copolymers, as well as pectin, dextrin and gelatin.

Other excipients include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

Instrumental Details:
X-Ray Powder Diffraction (P-XRD):
The X-ray powder diffraction spectrum was measured on a BRUKER AXS D8 FOCUS X-ray powder diffractometer equipped with a Cu-anode (copper-K$\alpha$ radiation). Approximately 1 gm of sample was gently flattered on a sample holder and scanned from 2 to 50 degrees 2-theta, at 0.03 degrees to theta per step and a step time of 38 seconds. The sample was simply placed on the sample holder. The sample was rotated at 30 rpm at a voltage 40 KV and current 35 mA.

Infra-Red Spectroscopy (FT-IR):
FT-IR spectroscopy was carried out with a Bruker vertex 70 spectrometer. For the production of the KBr compacts approximately 5 mg of sample was powdered with 200 mg of KBr. The spectra were recorded in transmission mode ranging from 3800 cm$^{-1}$ to 650 cm$^{-1}$.

Spray Drying:
Spray drying was performed on a Buchi Mini Spray dryer B-290 with an evaporating capacity of 1 L/hr for water and higher for organic solvents. The maximum temperature input was 220° C., the air flow was at a maximum of 35 m$^3$/hr, and the spray gas was compressed air or nitrogen at 200-1000 L/hr and 5-8 bar. The nozzle diameter was 0.7 mm (standard), and the nozzle cap was 1.4 mm and 1.5 mm.

REFERENCE EXAMPLE

Preparation of Solid State Form of Vilazodone Hydrochloride as Per the Process Reported in the Journal of Medicinal Chemistry, 2004, Vol. 47, No. 19, Pages 4684-4692 (see Column-1, Lines 47-57 of Page No. 4690)

Vilazodone free base (5.0 g) was dissolved in hot 2-propanol (215 ml) at 70° C. to form a clear solution. Activated carbon (1 g) was added to the solution, the resulting mass was maintained for 5 minutes at 70-75° C. and then filtered through hyflo bed. The resulting filtrate was cooled to room temperature, followed by slow addition of HCl-saturated 2-propanol solution at 25-35° C. Precipitation of vilazodone hydrochloride was occurred. After 15 minutes, the resulting precipitate was filtered at room temperature, the resulting wet cake was washed with diethyl ether (5 ml) and then dried at room temperature to produce 2.5 g of vilazodone hydrochloride (Purity by HPLC: 99.73%).

Characterization Data:
The resulting vilazodone hydrochloride solid is characterized by an X-ray powder diffraction pattern having peaks expressed as 2-theta angle positions at about 5.73, 8.79, 9.56, 10.07, 10.65, 11.05, 11.71, 13.73, 14.98, 17.64, 18.84, 20.49, 21.13, 22.05, 24.73, 25.47, 26.33, 27.48, 29.09, 30.28 and 31.60+0.2 degrees as shown in FIG. 16.

The following examples are given for the purpose of illustrating the present invention and should not be considered as limitation on the scope or spirit of the invention.

EXAMPLES

Example 1

Preparation of Amorphous Vilazodone Hydrochloride

Vilazodone hydrochloride (1 g, obtained according to the Reference Example) was dissolved in methanol (400 ml) at 60° C. and the resulting solution was subjected to carbon treatment by stirring the solution with activated carbon (0.4 g) for 10 minutes at 58-62° C. The resulting mixture was filtered through a hyflo bed and the resulting filtrate was cooled to 25-30° C. and then subjected to spray-drying in a mini spray dryer (Buchi model-290) at an inlet temperature of about 96-103° C. and an outlet temperature of about 56-65° C., and flow rate of 14 ml/minute using nitrogen gas to produce 0.75 g of amorphous Vilazodone hydrochloride as a white powder (Purity by HPLC: 99.73%).

Characterization Data:
The resulting amorphous vilazodone hydrochloride is characterized by an X-ray powder diffraction pattern, showing a plain halo with no well-defined peaks, as shown in FIG. 1; and further characterized by an infra red (FT-IR) spectrum having main bands at about 3180, 2941, 2844, 2679, 2586, 2460, 2344, 2216, 1669, 1599, 1580, 1472, 1445, 1397, 1322, 1245, 1222, 1168, 1098, 958, 941, 886, 809, 738, 683 and 668 cm$^{-1}$ as shown in FIG. 2.

Example 2

Preparation of Amorphous Vilazodone Hydrochloride

Vilazodone hydrochloride (1 g, obtained according to the Reference Example) was dissolved in methanol (400 ml) at 60° C. and the resulting solution was subjected to carbon treatment by stirring the solution with activated carbon (0.4 g) for 10 minutes at 58-62° C. The resulting mixture was filtered through a hyflo bed and the resulting filtrate was cooled to 25-30° C. and then subjected to spray-drying in a mini spray dryer (Buchi model-290) at an inlet temperature of about 78-81° C. and an outlet temperature of about 45-53° C., and flow rate of 16.8 ml/minute using nitrogen gas to produce 0.75 g of amorphous Vilazodone hydrochloride as a white powder (Purity by HPLC: 99.73%).
Characterization Data:

The resulting amorphous vilazodone hydrochloride is characterized by an X-ray powder diffraction pattern, showing a plain halo with no well-defined peaks, as shown in FIG. 3; and further characterized by an infra red (FT-IR) spectrum having main bands at about 3180, 2940, 2844, 2679, 2587, 2460, 2345, 2216, 1668, 1599, 1580, 1472, 1445, 1396, 1322, 1246, 1222, 1167, 1098, 958, 941, 886, 809, 738, 683 and 668 cm$^{-1}$ as shown in FIG. 4.

Example 3

Preparation of Amorphous Vilazodone Hydrochloride

Vilazodone hydrochloride (1 g, obtained according to the Reference Example) was dissolved in methanol (400 ml) at 60° C. and the resulting solution was subjected to carbon treatment by stirring the solution with activated carbon (0.4 g) for 10 minutes at 58-62° C. The resulting mixture was filtered through a hyflo bed and the resulting filtrate was cooled to 25-30° C. and then subjected to spray-drying in a mini spray dryer (Buchi model-290) at an inlet temperature of about 72-79° C. and an outlet temperature of about 41-54° C., and flow rate of 14 ml/minute using nitrogen gas to produce amorphous Vilazodone hydrochloride as a white powder (Purity by HPLC: 99.74%).

Example 4

Preparation of Amorphous Vilazodone Hydrochloride

Vilazodone hydrochloride (1 g, obtained according to the Reference Example) was dissolved in methanol (250 ml) at 60° C. and the resulting solution was filtered. The resulting clear filtrate was cooled to 25-30° C. and then subjected to spray-drying in a mini spray dryer (Buchi model-290) at an inlet temperature of about 75° C. and an outlet temperature of about 55° C., and flow rate of 14 ml/minute using nitrogen gas to produce amorphous vilazodone hydrochloride as a white powder (Purity by HPLC: 99.73%).

Example 5

Preparation of Amorphous Vilazodone Hydrochloride

Vilazodone hydrochloride (1 g, obtained according to the Reference Example) was dissolved in methanol (250 ml) at 60° C. and the resulting solution was filtered. The resulting clear filtrate was cooled to 25-30° C. and then subjected to spray-drying in a mini spray dryer (Buchi model-290) at an inlet temperature of about 74° C. and an outlet temperature of about 37° C., and flow rate of 16 ml/minute using nitrogen gas to produce amorphous vilazodone hydrochloride as a white powder (Purity by HPLC: 99.73%).

Example 6

Preparation of Amorphous Co-Precipitate of Vilazodone Hydrochloride with Polyvinylpyrrolidone (1:10)

Vilazodone hydrochloride (0.5 g, obtained according to the Reference Example) was added to methanol (400 ml) at 25-30° C., the contents were stirred for 5 minutes at the same temperature, followed by heating at 50° C. to form a clear solution. The resulting solution was cooled to room temperature (25-35° C.) and then polyvinylpyrrolidone (5 g) was added at the same temperature to obtain a clear solution. The resulting solution was stirred for 30 minutes at room temperature, followed by removal of solvent by distillation under vacuum at 65-70° C. to produce 5.5 g of amorphous co-precipitate of vilazodone hydrochloride with polyvinylpyrrolidone in a ratio of 1:10 (Purity by HPLC: 99.72%).
Characterization Data:

The resulting amorphous co-precipitate of vilazodone hydrochloride with polyvinylpyrrolidone (1:10) is characterized by an X-ray powder diffraction pattern, showing a plain halo with no well-defined peaks, as shown in FIG. 7; and further characterized by an infra red (FT-IR) spectrum having main bands at about 3446, 2956, 2923, 2217, 1652, 1495, 1464, 1440, 1423, 1373, 1318, 1289, 1273, 1227, 1169, 1074, 1018, 960, 935, 891, 844, 820 and 737±2 cm$^{-1}$ as shown in FIG. 8.

Example 7

Preparation of Amorphous Co-precipitate of Vilazodone Hydrochloride with Polyvinylpyrrolidone (1:5)

Vilazodone hydrochloride (0.5 g, obtained according to the Reference Example) was added to methanol (200 ml) at 25-30° C., the contents were stirred for 5 minutes at the same temperature, followed by heating at 50° C. to form a clear solution. The resulting solution was cooled to room temperature (25-35° C.) and then polyvinylpyrrolidone (2.5 g) was added at the same temperature to obtain a clear solution. The resulting solution was stirred for 1 hour at room temperature, followed by removal of solvent by distillation under vacuum at 65-70° C. to produce 3 g of amorphous co-precipitate of vilazodone hydrochloride with polyvinylpyrrolidone in a ratio of 1:5 (Purity by HPLC: 99.73%).
Characterization Data:

The resulting amorphous co-precipitate of vilazodone hydrochloride with polyvinylpyrrolidone (1:5) is characterized by an X-ray powder diffraction pattern, showing a plain halo with no well-defined peaks, as shown in FIG. 9; and further characterized by an infra red (FT-IR) spectrum having main bands at about 3446, 2955, 2923, 2217, 1662, 1495, 1464, 1440, 1423, 1373, 1319, 1290, 1274, 1227, 1169, 1074, 1018, 960, 938, 891, 844, 820 and 736±2 cm$^{-1}$ as shown in FIG. 10.

Example 8

Preparation of Amorphous Co-precipitate of Vilazodone Hydrochloride with Hypromellose Phthalate (1:10)

Vilazodone hydrochloride (0.5 g, obtained according to the Reference Example) was added to methanol (400 ml) at 25-30° C., the contents were stirred for 5 minutes at the same temperature, followed by heating at 50° C. to form a clear solution. The resulting solution was cooled to room temperature (25-35° C.) and then hypromellose phthalate (5 g) was added at the same temperature to obtain a clear solution. The resulting solution was stirred for 30 minutes at room temperature, followed by removal of solvent by distillation under vacuum at 65-70° C. to produce 5.5 g of amorphous co-precipitate of vilazodone hydrochloride with hypromellose phthalate in a ratio of 1:10 (Purity by HPLC: 99.73%).
Characterization Data:
The resulting amorphous co-precipitate of vilazodone hydrochloride with hypromellose phthalate (1:10) is characterized by an X-ray powder diffraction pattern, showing a plain halo with no well-defined peaks, as shown in FIG. 11; and further characterized by an infra red (FT-IR) spectrum having main bands at about 3454, 2925, 2853, 2219, 1727, 1600, 1581, 1492, 1461, 1451, 1379, 1290, 1262, 1216, 1124, 1071, 952, 942, 889, 857, 819 and 741±2 cm$^{-1}$ as shown in FIG. 12.

Example 9

Preparation of Amorphous Co-Precipitate of Vilazodone Hydrochloride with Hydroxypropyl Cellulose (1:15)

Vilazodone hydrochloride (0.5 g, obtained according to the Reference Example) was added to methanol (100 ml) at 25-30° C., the contents were stirred for 5 minutes at the same temperature, followed by heating at 50° C. to form a clear solution. The resulting solution was cooled to room temperature (25-35° C.) and then hydroxypropyl cellulose (7.5 g) was added at the same temperature to obtain a clear solution. The resulting solution was stirred for 30 minutes at room temperature, followed by removal of solvent by distillation under vacuum at 65-70° C. to produce 8 g of amorphous co-precipitate of vilazodone hydrochloride with hydroxypropyl cellulose in a ratio of 1:15 (Purity by HPLC: 99.71%).
Characterization Data:
The resulting amorphous co-precipitate of vilazodone hydrochloride with hydroxypropyl cellulose (1:15) is characterized by an X-ray powder diffraction pattern as shown in FIG. 13.

Example 10

Preparation of Amorphous Co-precipitate of Vilazodone Hydrochloride with Hydroxypropyl Cellulose (1:10)

Vilazodone hydrochloride (0.5 g, obtained according to the Reference Example) was added to methanol (200 ml) at 25-30° C., the contents were stirred for 5 minutes at the same temperature, followed by heating at 50° C. to form a clear solution. The resulting solution was cooled to room temperature (25-35° C.) and then hydroxypropyl cellulose (5 g) was added at the same temperature to obtain a clear solution. The resulting solution was stirred for 30 minutes at room temperature, followed by removal of solvent by distillation under vacuum at 65-70° C. to produce 5.5 g of amorphous co-precipitate of vilazodone hydrochloride with hydroxypropyl cellulose in a ratio of 1:10 (Purity by HPLC: 99.72%).
Characterization Data:
The resulting amorphous co-precipitate of vilazodone hydrochloride with hydroxypropyl cellulose (1:15) is characterized by an X-ray powder diffraction pattern as shown in FIG. 14.

Example 11

Preparation of Amorphous Co-Precipitate of Vilazodone Hydrochloride with Hydroxypropyl Cellulose (1:2)

Vilazodone hydrochloride (0.5 g, obtained according to the Reference Example) was added to methanol (400 ml) at 25-30° C., the contents were stirred for 5 minutes at the same temperature, followed by heating at 50° C. to form a clear solution. The resulting solution was cooled to room temperature (25-35° C.) and then hydroxypropyl cellulose (1 g) was added at the same temperature to obtain a clear solution. The resulting solution was stirred for 30 minutes at room temperature, followed by removal of solvent by distillation under vacuum at 65-70° C. to produce 1.5 g of amorphous co-precipitate of vilazodone hydrochloride with hydroxypropyl cellulose in a ratio of 1:2 (Purity by HPLC: 99.73%).
Characterization Data:
The resulting amorphous co-precipitate of vilazodone hydrochloride with hydroxypropyl cellulose (1:15) is characterized by an X-ray powder diffraction pattern as shown in FIG. 15.

Unless otherwise indicated, the following definitions are set forth to illustrate and define the meaning and scope of the various terms used to describe the invention herein.

The term "micronization" used herein means a process or method by which the size of a population of particles is reduced.

As used herein, the term "micron" or "μm" both are equivalent and refer to "micrometer" which is 1×10$^{-6}$ meter.

As used herein, "Particle Size Distribution (P.S.D)" means the cumulative volume size distribution of equivalent spherical diameters as determined by laser diffraction in Malvern Master Sizer 2000 equipment or its equivalent.

The important characteristics of the PSD are the ($D_{90}$), which is the size, in microns, below which 90% of the particles by volume are found, and the ($D_{50}$), which is the size, in microns, below which 50% of the particles by volume are found. Thus, a $D_{90}$ or d(0.9) of less than 300 microns means that 90 volume-percent of the particles in a composition have a diameter less than 300 microns.

The term "coprecipitate or co-precipitate" as used herein refers to compositions comprising amorphous vilazodone hydrochloride together with at least one pharmaceutically acceptable excipient, being prepared by removing solvent from a solution containing both of them.

The term "pharmaceutically acceptable" means that which is useful in preparing a pharmaceutical composition that is generally non-toxic and is not biologically undesirable, and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

The term "therapeutically effective amount" as used herein means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The term "delivering" as used herein means providing a therapeutically effective amount of an active ingredient to a particular location within a host causing a therapeutically effective blood concentration of the active ingredient at the particular location. This can be accomplished, e.g., by topical, local or by systemic administration of the active ingredient to the host, e.g., human, animal, etc.

The term "buffering agent" as used herein is intended to mean a compound used to resist a change in pH upon dilution or addition of acid of alkali. Such compounds include, by way of example and without limitation, potassium metaphosphate, potassium phosphate, monobasic sodium acetate and sodium citrate anhydrous and dihydrate and other such materials known to those of ordinary skill in the art.

The term "sweetening agent" as used herein is intended to mean a compound used to impart sweetness to a formulation. Such compounds include, by way of example and without limitation, aspartame, dextrose, glycerin, mannitol, saccharin sodium, sorbitol, sucrose, fructose and other such materials known to those of ordinary skill in the art.

The term "binders" as used herein is intended to mean substances used to cause adhesion of powder particles in granulations. Such compounds include, by way of example and without limitation, acacia, alginic acid, tragacanth, carboxymethylcellulose sodium, polyvinylpyrrolidone, compressible sugar, ethylcellulose, gelatin, liquid glucose, methylcellulose, pregelatinized starch, starch, polyethylene glycol, guar gum, polysaccharide, bentonites, sugars, invert sugars, poloxamers, collagen, albumin, celluloses in non-aqueous solvents, polypropylene glycol, polyoxyethylene-polypropylene copolymer, polyethylene ester, polyethylene sorbitan ester, polyethylene oxide, microcrystalline cellulose, combinations thereof and other material known to those of ordinary skill in the art.

The term "diluents" or "filler" as used herein is intended to mean inert substances used as fillers to create the desired bulk, flow properties, and compression characteristics in the preparation of solid dosage formulations. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

The term "glidant" as used herein is intended to mean agents used in solid dosage formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

The term "lubricant" as used herein is intended to mean substances used in solid dosage formulations to reduce friction during compression of the solid dosage. Such compounds include, by way of example and without limitation, calcium stearate, magnesium stearate, mineral oil, stearic acid, zinc stearate, combinations thereof and other such materials known to those of ordinary skill in the art.

The term "disintegrant" as used herein is intended to mean a compound used in solid dosage formulations to promote the disruption of the solid mass into smaller particles which are more readily dispersed or dissolved. Exemplary disintegrants include, by way of example and without limitation, starches such as corn starch, potato starch, pregelatinized, sweeteners, clays, such as bentonite, microcrystalline cellulose, carsium, alginates, sodium starch glycolate, gums such as agar, guar, locust bean, karaya, pectin, tragacanth, combinations thereof and other such materials known to those of ordinary skill in the art.

The term "wetting agent" as used herein is intended to mean a compound used to aid in attaining intimate contact between solid particles and liquids. Exemplary wetting agents include, by way of example and without limitation, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, polyethylene glycols, polyoxyethylene stearates colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, and polyvinylpyrrolidone (PVP).

All ranges disclosed herein are inclusive and combinable. While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

We claim:

1. An amorphous co-precipitate comprising vilazodone hydrochloride and a pharmaceutically acceptable excipient, wherein the pharmaceutically acceptable excipient is selected from the group consisting of polyvinylpyrrolidone, hydroxypropyl cellulose, hydroxypropyl methylcellulose and hypromellose phthalate, wherein the amorphous co-precipitate is:
   a) the amorphous co-precipitate of vilazodone hydrochloride with polyvinylpyrrolidone in a ratio of 1:10 which is characterized by a powder XRD pattern, showing no well-defined peaks, substantially in accordance with FIG. 7;

b) the amorphous co-precipitate of vilazodone hydrochloride with polyvinylpyrrolidone in a ratio of 1:5 which is characterized by a powder XRD pattern, showing no well-defined peaks, substantially in accordance with FIG. 9;

c) the amorphous co-precipitate of vilazodone hydrochloride with hypromellose phthalate in a ratio of 1:10 which is characterized by a powder XRD pattern, showing no well-defined peaks, substantially in accordance with FIG. 11; and d) the amorphous co-precipitate of vilazodone hydrochloride with hydroxypropyl cellulose is characterized by a powder XRD pattern, showing no well-defined peaks, substantially in accordance with FIG. 13, FIG. 14 or FIG. 15.

2. An amorphous co-precipitate comprising vilazodone hydrochloride and a pharmaceutically acceptable excipient, wherein the pharmaceutically acceptable excipient is selected from the group consisting of polyvinylpyrrolidone, hydroxypropyl cellulose, hydroxypropyl methylcellulose and hypromellose phthalate, wherein the amorphous co-precipitate is:

a) the amorphous co-precipitate of vilazodone hydrochloride with polyvinylpyrrolidone in a ratio of 1:10 which is further characterized by an infrared (FT-IR) spectrum having main bands at about 3446, 2956, 2923, 2217, 1652, 1495, 1464, 1440, 1423, 1373, 1318, 1289, 1273, 1227, 1169, 1074, 1018, 960, 935, 891, 844, 820 and 737±2 cm$^{-1}$ substantially in accordance with FIG. 8;

b) the amorphous co-precipitate of vilazodone hydrochloride with polyvinylpyrrolidone in a ratio of 1:5 which is further characterized by an infrared (FT-IR) spectrum having main bands at about 3446, 2955, 2923, 2217, 1662, 1495, 1464, 1440, 1423, 1373, 1319, 1290, 1274, 1227, 1169, 1074, 1018, 960, 938, 891, 844, 820 and 736±2 cm$^{-1}$ substantially in accordance with FIG. 10; and c) the amorphous co-precipitate of vilazodone hydrochloride with hypromellose phthalate in a ratio of 1:10 which is further characterized by an infrared (FT-IR) spectrum having main bands at about 3454, 2925, 2853, 2219, 1727, 1600, 1581, 1492, 1461, 1451, 1379, 1290, 1262, 1216, 1124, 1071, 952, 942, 889, 857, 819 and 741±2 cm$^{-1}$ substantially in accordance with FIG. 12.

3. A pharmaceutical composition comprising an amorphous co-precipitate comprising vilazodone hydrochloride and a pharmaceutically acceptable excipients as claimed in claim 1, and one or more pharmaceutically acceptable excipients.

4. A process for the preparation of the amorphous co-precipitate of claim 1, comprising:

a) providing a solution of vilazodone hydrochloride and a pharmaceutically acceptable excipient in a solvent selected from the group consisting of water, an alcohol, an ester, a polar aprotic solvent, and mixtures thereof;

b) optionally, filtering the solvent solution to remove insoluble matter; and c) substantially removing the solvent from the solution to produce the amorphous co-precipitate of vilazodone hydrochloride with the pharmaceutically acceptable excipient;

wherein the pharmaceutically acceptable excipient used in step-(a) is selected from the group consisting of polyvinylpyrrolidone, maltodextrin, hydroxypropyl cellulose, hydroxypropyl methylcellulose and hypromellose phthalate.

5. The process of claim 4, wherein the solvent used in step-(a) is selected from the group consisting of water, methanol, ethanol, isopropyl alcohol, and mixtures thereof; and wherein the removal of the solvent in step-(c) is accomplished by distillation or complete evaporation of the solvent, spray drying, vacuum drying, lyophilization or freeze drying, agitated thin-film drying, or a combination thereof.

6. The process of claim 5, wherein the solvent used in step-(a) is methanol; and wherein the removal of the solvent in step-(c) is accomplished by distillation, wherein the distillation process is performed under reduced pressure and at a temperature of about 50° C. to about 110° C.

* * * * *